(12) United States Patent
Ueya

(10) Patent No.: US 10,466,235 B2
(45) Date of Patent: Nov. 5, 2019

(54) SOLID SUPPORT, LIGAND-BOUND SOLID SUPPORT, DETECTION OR SEPARATION METHOD FOR TARGET SUBSTANCE, SOLID SUPPORT PRODUCTION METHOD, AND LIGAND-BOUND SOLID SUPPORT PRODUCTION METHOD

(71) Applicants: JSR CORPORATION, Minato-ku (JP); JSR LIFE SCIENCES CORPORATION, Minato-ku (JP)

(72) Inventor: Yuuichi Ueya, Minato-ku (JP)

(73) Assignees: JSR CORPORATION, Minato-ku (JP); JSR Life Sciences Corporation, Minato-ku (JP)

( * ) Notice: Subject to any disclaimer, the term of this patent is extended or adjusted under 35 U.S.C. 154(b) by 541 days.

(21) Appl. No.: 15/123,529

(22) PCT Filed: Mar. 4, 2015

(86) PCT No.: PCT/JP2015/056306
§ 371 (c)(1),
(2) Date: Feb. 1, 2017

(87) PCT Pub. No.: WO2015/133507
PCT Pub. Date: Sep. 11, 2015

(65) Prior Publication Data
US 2017/0146528 A1    May 25, 2017

(30) Foreign Application Priority Data
Mar. 5, 2014   (JP) ................. 2014-042305

(51) Int. Cl.
*G01N 33/543*    (2006.01)
*C08F 292/00*    (2006.01)
(Continued)

(52) U.S. Cl.
CPC ......... *G01N 33/54353* (2013.01); *C08F 8/14* (2013.01); *C08F 212/08* (2013.01);
(Continued)

(58) Field of Classification Search
CPC .......... G01N 33/54353; G01N 33/543; G01N 33/54326; G01N 33/553; G01N 27/44704;
(Continued)

(56) References Cited

U.S. PATENT DOCUMENTS 4,415,631 A  11/1983 Schutijser
4,724,207 A   2/1988 Hou et al.
(Continued)

FOREIGN PATENT DOCUMENTS

CN   101341408 A   1/2009
CN   101511892 A   8/2009
(Continued)

OTHER PUBLICATIONS

Extended European Search Report dated Nov. 7, 2017 in corresponding European Patent Application No. 15757985.5, 11 pages.
(Continued)

*Primary Examiner* — Dennis White
(74) *Attorney, Agent, or Firm* — Oblon, McClelland, Maier & Neustadt, L.L.P.

(57) ABSTRACT

To provide a solid-phase carrier to which impurities are hard to nonspecifically adsorb. A solid-phase carrier, formed by binding a chain polymer, wherein the chain polymer comprises a random polymer structure containing a first structural unit having a reactive functional group, and a second structural unit having no reactive functional group or having a reactive functional group having a reactivity lower than that of the reactive functional group of the first structural unit, and the content ratio of the number of moles "a" of the reactive functional group contained in the first structural unit to the number of moles "b" of the entire structural unit contained in the chain polymer, (a/b), is from 0.01 to 0.7.

20 Claims, 2 Drawing Sheets

(51) Int. Cl.
G01N 27/447 (2006.01)
C08F 212/08 (2006.01)
G01N 33/553 (2006.01)
C08F 8/14 (2006.01)

(52) U.S. Cl.
CPC ..... *C08F 292/00* (2013.01); *G01N 27/44704* (2013.01); *G01N 33/543* (2013.01); *G01N 33/54326* (2013.01); *G01N 33/553* (2013.01); *C08F 2810/50* (2013.01)

(58) Field of Classification Search
CPC ........ C08F 8/14; C08F 212/08; C08F 292/00; C08F 2810/50
See application file for complete search history.

(56) References Cited

U.S. PATENT DOCUMENTS

| | | |
|---|---|---|
| 2007/0099814 A1 | 5/2007 | Tamori et al. |
| 2008/0139399 A1 | 6/2008 | Fonnum et al. |
| 2010/0152708 A1 | 6/2010 | Li et al. |
| 2010/0181254 A1 | 7/2010 | Graalfs |
| 2011/0006245 A1 | 1/2011 | Handa et al. |
| 2013/0251636 A1 | 9/2013 | Tago et al. |
| 2014/0183136 A1 | 7/2014 | Graalfs et al. |

FOREIGN PATENT DOCUMENTS

| | | |
|---|---|---|
| CN | 101678318 A | 3/2010 |
| JP | 57-38937 A | 3/1982 |
| JP | 61-166861 A | 7/1986 |
| JP | 2006-131771 A | 5/2006 |
| JP | 2006-328309 A | 12/2006 |
| JP | 2007-224213 A | 9/2007 |
| JP | 2009-542862 A | 12/2009 |
| JP | 2010-528271 A | 8/2010 |
| JP | 2010-260877 A | 11/2010 |
| JP | 2012-82328 A | 4/2012 |
| WO | WO 2008/145270 A1 | 12/2008 |
| WO | WO 2009/081700 A1 | 7/2009 |
| WO | WO 2012/073588 A1 | 6/2012 |
| WO | WO 2013/047527 A1 | 4/2013 |

OTHER PUBLICATIONS

Combined Office Action and Search Report dated Jan. 26, 2018 in Chinese Patent Application No. 201580011386.9 with unedited computer generated English translation of the Office Action and English translation of categories of cited documents, 34 pages.

Office Action dated Jun. 22, 2018 in corresponding European Patent Application No. 15757985.5, 5 pages.

Jiang S, et al., "Ultralow-fouling, Functionalizable, and Hydrolyzable Zwitterionic Materials and their Derivatives for Biological Applications", Advanced Materials, DOI: 10.1002/adma.200901407, 22, 2010, pp. 920-932.

International Search Report dated Jun. 2. 2015, in PCT/JP2015/056306 filed Mar. 4. 2015.

SOLID SUPPORT, LIGAND-BOUND SOLID SUPPORT, DETECTION OR SEPARATION METHOD FOR TARGET SUBSTANCE, SOLID SUPPORT PRODUCTION METHOD, AND LIGAND-BOUND SOLID SUPPORT PRODUCTION METHOD

TECHNICAL FIELD

The present invention relates to a solid-phase carrier, a ligand-bound solid-phase carrier, a method for detecting or separating a target substance, a method for producing the solid-phase carrier, and a method for producing the ligand-bound solid-phase carrier.

BACKGROUND ART

Some of diagnostic agents and diagnostic kits for diagnosing diseases such as cancer and infectious diseases use a solid-phase carrier such as magnetic particles. Such solid-phase carrier usually binds a ligand such as an antibody or oligonucleotide and is used. For example, the antibody and oligonucleotide specifically bind to, for example, a specific antigen or nucleic acid. Thus, for example, the presence or absence and concentration of a diagnostic marker in a sample can be detected. Also, it is possible to isolate, for example, specific cells such as cancer cells, by the same method.

With the improvement and development of a solid-phase carrier, detection sensitivity has been improved year by year, and the detectable diagnostic markers and the kind of cells that can be isolated have been increased. For example, Patent Literature 1 describes carrier particles of which surface is covered with a polymer layer that can bind to a probe. This polymer is constituted by a monomer unit having a carboxy group on a side chain and a monomer unit having a 2, 3-dihydroxypropyl group on a side chain.

In addition, Patent Literature 2 describes a multiblock vinyl polymer, i.e., polymer particles in which a block copolymer binds to the surface.

CITATION LIST

Patent Literatures

Patent Literature 1: JP 2007-224213 A
Patent Literature 2: JP 2009-542862 W

SUMMARY OF INVENTION

Technical Problem

However, when the present inventors have tested a technology described in Patent Literature 2, it found that nonspecific adsorption of impurities to a carrier is larger than expected, and impurities adsorb to many of reactive functional groups used in binding with a ligand. The present inventors thought that this is attributable to localization of a reactive functional group causing nonspecific adsorption in a block copolymer.

An object of the present invention is to provide a solid-phase carrier to which impurities are hard to nonspecifically adsorb.

Solution to Problem

Under the above circumstances, the present inventors intensively studied and consequently found that impurities are hard to nonspecifically adsorb to a solid-phase carrier, formed by binding a chain polymer, including a random polymer structure containing a first structural unit having a reactive functional group, and a specific second structural unit, and having a content ratio of the number of moles "a" of the reactive functional group contained in the first structural unit to the number of moles "b" of the entire structural unit contained in the chain polymer, (a/b), of from 0.01 to 0.7, thereby completing the present invention.

That is, the present invention provides the following <1> to <5>.

<1> A solid-phase carrier, formed by binding a chain polymer, wherein the chain polymer includes a random polymer structure containing a first structural unit having a reactive functional group, and a second structural unit having no reactive functional group or having a reactive functional group having a reactivity lower than that of the reactive functional group of the first structural unit, and the content ratio of the number of moles "a" of the reactive functional group contained in the first structural unit to the number of moles "b" of the entire structural unit contained in the chain polymer, (a/b), is from 0.01 to 0.7.

<2> A ligand-bound solid-phase carrier, formed by binding a ligand to the solid-phase carrier as defined in <1> above.

<3> A method for detecting or separating a target substance in a sample, the method using the ligand-bound solid-phase carrier as defined in <2> above.

<4> A method, for producing a solid-phase carrier, the method including the following Step 1 and Step 2:

(Step 1) a step of preparing a carrier having a polymerization initiating group at least on the surface, and (Step 2) a step of forming, from the polymerization initiating group as a starting point, a chain polymer including a random polymer structure containing a first structural unit having a reactive functional group, and a second structural unit having no reactive functional group or having a reactive functional group having a reactivity lower than that of the reactive functional group of the first structural unit, such that the content ratio of the number of moles "a" of the reactive functional group contained in the first structural unit to the number of moles "b" of the entire structural unit contained in the chain polymer, (a/b), is from 0.01 to 0.7.

<5> A method for producing a ligand-bound solid-phase carrier, the method including a step of binding a ligand to the reactive functional group contained in the first structural unit of the solid-phase carrier produced in the production method as defined in <4> above.

Advantageous Effects of Invention

According to the present invention, a solid-phase carrier to which impurities are hard to nonspecifically adsorb can be provided. Specifically, in the solid-phase carrier of the present invention, impurities are hard to nonspecifically adsorb to a reactive functional group used in binding with a ligand.

DESCRIPTION OF EMBODIMENTS

Figure 1:
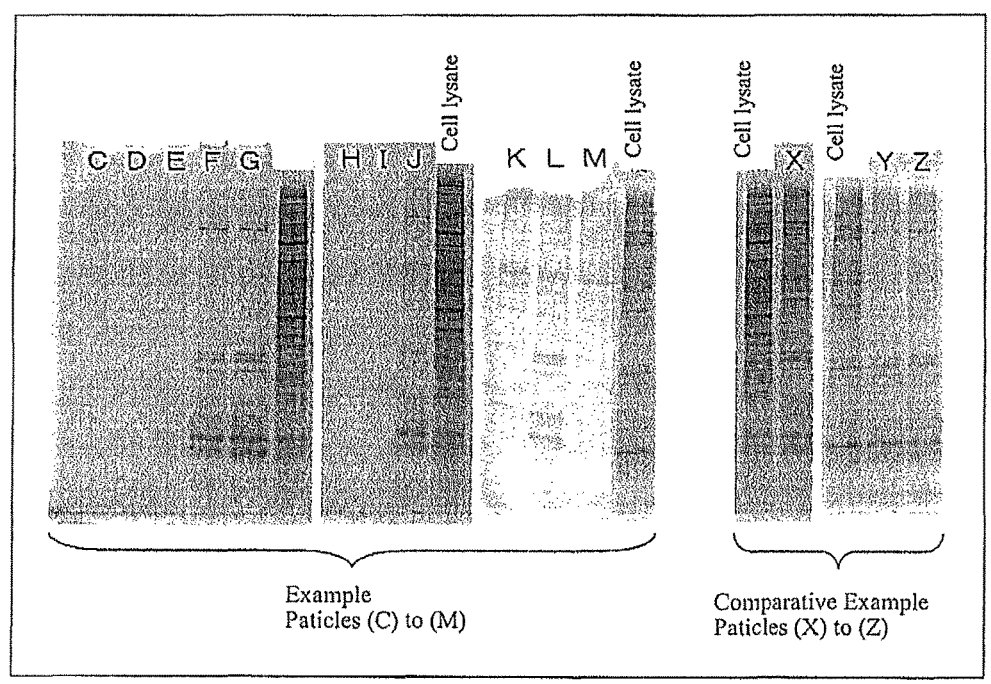
FIG. 1 is an electrophoretic photograph. The same figure shows a result of carrying out a comparative experiment of an effect of suppressing nonspecific adsorption of magnetic particles of examples and comparative examples.

Hereinbelow, the present invention will be described in detail. Herein, the description showing the numerical range of, for example, a to b, is synonymous with a or more and b or less, and includes a and b in the range.

<Solid-Phase Carrier>

The solid-phase carrier of the present invention, formed by binding a chain polymer, is characterized by the chain polymer includes a random polymer structure containing a first structural unit having a reactive functional group, and a second structural unit having no reactive functional group or having a reactive functional group having a reactivity lower than that of the reactive functional group of the first structural unit, and the content ratio of the number of moles "a" of the reactive functional group contained in the first structural unit to the number of moles "b" of the entire structural unit contained in the chain polymer, (a/b), is from 0.01 to 0.7.

(First Structural Unit)

The first structural unit has a reactive functional group (hereinbelow, a reactive functional group of a first structural unit is also referred to as a first reactive functional group). As the first structural unit, a structural unit having a first reactive functional group on a side chain is preferred. The number of the first reactive functional group is preferably 1 to 3 and more preferably 1 per the above structural unit.

As the first structural unit, a structural unit derived from an ethylenically unsaturated monomer having a first reactive functional group is preferred. Herein, the ethylenically unsaturated monomer refers to a monomer having an ethylenically unsaturated bond such as a vinyl group, an allyl group, a (meth)acryloxy group, or a (meth)acrylamide group.

Also, examples of the first structural unit include a structural unit derived from a (meth)acrylic acid or a salt thereof, a structural unit derived from a (meth)acrylate monomer having a first reactive functional group, a structural unit derived from a (meth)acrylamide monomer having a first reactive functional group, and a structural unit derived from a styrene monomer having a first reactive functional group. Among them, a structural unit derived from a (meth)acrylic acid or a salt thereof, a structural unit derived from a (meth)acrylate monomer having a first reactive functional group, and a structural unit derived from a (meth)acrylamide monomer having a first reactive functional group are preferred, and a structural unit derived from a (meth)acrylate monomer having a first reactive functional group and a structural unit derived from a (meth)acrylamide monomer having a first reactive functional group are more preferred, from the view point of the suppression of nonspecific adsorption.

Also, the first reactive functional group is not particularly limited as long as it is reactive with a ligand. It includes a carboxy group, a tosyl group, an amino group, an epoxy group, an acyl group, an azide group, a maleimide group, and an activated ester group, and the first structural unit may have one or two or more of these groups. Among these groups, a carboxy group, a tosyl group, an amino group and an epoxy group are preferred from the view point of preventing a bound ligand from coming off and from the point that, when a biomolecule such as a protein or a nucleic acid is used as a ligand, the biomolecule can bind to a solid-phase carrier using a functional group which the ligand originally has, and a carboxy group is more preferred, for example, from the point that a ligand is easily allowed to simply and quickly bind to a solid-phase carrier.

Also, the content of the first reactive functional group per g of solid content in a solid-phase carrier is preferably 1 µmol or more, more preferably 10 µmol or more, further preferably 20 µmol or more, and especially preferably 25 µmol or more, from the view point of the amount of bound ligand and from the view point of achieving both an increase in sensitivity and a decrease in noise in detection, and is also preferably 500 µmol or less, more preferably 400 µmol or less, further preferably 200 µmol or less, further preferably 180 µmol or less, and especially preferably 135 µmol or less, from the view point of suppressing nonspecific adsorption.

The content of the first reactive functional group can be, for example, when the first reactive functional group is a carboxy group, measured by, for example, conductometry, and specifically can be measured in accordance with a method described in the examples mentioned below. In addition, when the first reactive functional group is a tosyl group, the content can be obtained by, for example, measuring an absorption of the ultraviolet-visible light of a tosyl group introduced into a solid-phase carrier, and when the first reactive functional group is an amino group, the content can be obtained by, for example, allowing an amino group to react with N-succinimidyl-3-(2-pyridyldithio)propionate, followed by reduction, and measuring the absorbance of free thiopyridyl group.

The value obtained by dividing the surface area of the solid-phase carrier by the content of the first reactive functional group is preferably 0.4 $Å^2$/reactive functional group or more, more preferably 0.6 $Å^2$/reactive functional group or more, further preferably 1.2 $Å^2$/reactive functional group or more, and especially preferably 1.8 $Å^2$/reactive functional group or more, and is preferably 220 $Å^2$/reactive functional group or less, more preferably 22 $Å^2$/reactive functional group or less, further preferably 20 $Å^2$/reactive functional group or less, further preferably 9 $Å^2$/reactive functional group or less, and especially preferably 7.4 $Å^2$/reactive functional group or less, from the view point of the amount of bound ligand and from the view point of suppressing nonspecific adsorption.

Herein, the value obtained by dividing the surface area of the solid-phase carrier by the content of the first reactive functional group is also referred to as "parking area". Parking area is an index showing an area occupied by one molecule of reactive functional group on the surface of the solid-phase carrier. Generally, the amount of bound ligand is inversely proportional to the numerical value of the parking area, and the larger the parking area, the smaller the amount of bound ligand. Also, the surface area of the solid-phase carrier means a surface area of the carrier before binding of the chain polymer.

Specific preferred examples of the first structural unit include structural units represented by the following formula (1).

wherein $R^1$ represents a hydrogen atom or a methyl group, $R^2$ represents —O—*, —(C=O)—O—*, —(C=O)—NR$^4$—* ($R^4$ represents a hydrogen atom or an organic group having 1 to 10 carbon atoms, and * represents a position bound to $R^3$ in the formula (1)) or a phenylene group, and when $R^2$ is —(C=O)—O—*, $R^3$ represents a hydrogen atom or an organic group having a first reactive functional group, and when $R^2$ is —O—*, —(C=O)—NR$^4$—* or a phenylene group, $R^3$ represents an organic group having a first reactive functional group.

In the formula (1), $R^2$ is preferably —(C=O)—O—* or —(C=O)—NR$^4$—*, from the view point of increasing affinity for water and suppressing nonspecific adsorption.

$R^4$ represents a hydrogen atom or an organic group having 1 to 10 carbon atoms.

The number of carbon atoms of the organic group represented by $R^4$ is preferably from 1 to 8, more preferably from 1 to 6, and especially preferably from 1 to 3. Also, the organic group is preferably a hydrocarbon group, and more preferably an aliphatic hydrocarbon group. The aliphatic hydrocarbon group may be a straight chain or a branched chain, and specific examples thereof include alkyl groups such as a methyl group, an ethyl group, an n-propyl group, an isopropyl group, an n-butyl group, an isobutyl group, a sec-butyl group, a tert-butyl group, a pentyl group, a hexyl group, a heptyl group, and an octyl group.

Among $R^4$s as above, a hydrogen atom is preferred.

Also, the organic group having a reactive functional group represented by $R^3$ is preferably an organic group represented by the following formula (2). The first reactive functional group in $R^3$ is the same as above.

*—R$^5$—Y  (2)

wherein $R^5$ represents a divalent organic group, Y represents a first reactive functional group, and * represents a position bound to $R^2$ in the formula (1).

The divalent organic group represented by $R^5$ includes divalent hydrocarbon groups, and groups having one or more selected from the group consisting of an ether bond, an imino group, an amide bond and an ester bond between carbon-carbon atoms in a divalent hydrocarbon group having 2 or more carbon atoms.

When the divalent organic group is a divalent hydrocarbon group, the number of carbon atoms is preferably from 1 to 10, more preferably from 1 to 8, and especially preferably from 1 to 6. Meanwhile, when the divalent organic group is a group having one or more selected from the group consisting of an ether bond, an imino group, an amide bond and an ester bond between carbon-carbon atoms in a divalent hydrocarbon group having 2 or more carbon atoms, the number of carbon atoms of the divalent hydrocarbon group in such a group is preferably from 2 to 10, more preferably from 2 to 8, and especially preferably from 2 to 6.

As the "divalent hydrocarbon group" in $R^5$, a divalent aliphatic hydrocarbon group is preferred. The divalent aliphatic hydrocarbon group may be a straight chain or a branched chain.

As the above divalent aliphatic hydrocarbon group, an alkanediyl group is preferred, and specific examples thereof include a methane-1,1-diyl group, an ethane-1,1-diyl group, an ethane-1,2-diyl group, a propane-1,1-diyl group, a propane-1,2-diyl group, a propane-1,3-diyl group, propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, and a hexane-1,6-diyl group.

As the group having one or more selected from the group consisting of an ether bond, an imino group, an amide bond and an ester bond between carbon-carbon atoms in a divalent hydrocarbon group having 2 or more carbon atoms, a group having an ester bond between carbon-carbon atoms in the divalent hydrocarbon group having 2 or more carbon atoms is preferred, and a divalent group represented by —R$^a$—O(C=O)—R$^b$—*, wherein R$^a$ and R$^b$ independently represent an alkanediyl group having 2 to 4 carbon atoms, and * represents a position bound to Y in the formula (2), is more preferred, for example, from the view point of easily obtaining a chain polymer. The number of carbon atoms in an alkanediyl group is preferably 2 or 3, and more preferably 2. The alkanediyl group may be a straight chain or a branched chain, and examples thereof include an ethane-1,2-diyl group, a propane-1,2-diyl group, and a propane-1,3-diyl group.

As the above combination of $R^2$ and $R^3$, a combination of —(C=O)—O—* as $R^2$ and a hydrogen atom or an organic group having a reactive functional group as $R^3$, and a combination of —(C=O)—NR$^4$—* as $R^2$ and an organic group having a reactive functional group as $R^3$ are preferred, and a combination of —(C=O)—O—* or —(C=O)—NR$^4$—* as $R^2$ and an organic group having a reactive functional group as $R^3$ is more preferred.

The content of the first structural unit is preferably 1 to 70% by mass, more preferably 5 to 70% by mass, and especially preferably 5 to 35% by mass, based on the entire amount of the random polymer structure.

The content of the first structural unit may be measured by using, for example, NMR.

(Second Structural Unit)

The second structural unit does not have a reactive functional group or has a reactive functional group having a reactivity lower than that of the reactive functional group of the first structural unit (hereinbelow, this reactive functional group is also referred to as a second reactive functional group).

The above second reactive functional group has a reactivity lower than that of the first reactive functional group. The affinity constant or reaction rate constant is an index of this reactivity. Specifically, when the affinity constant or reaction rate constant to the ligand of the second reactive functional group is lower than the affinity constant or reaction rate constant to the ligand of the first reactive functional group, the reactivity of the second reactive functional group means to be lower than the reactivity of the first reactive functional group. Based on the above viewpoint, the second reactive functional group is different from the first reactive functional group, whereby it is needless to say that the second reactive functional group may have low reactivity, and for example, the reactivity of the second reactive functional group may be suppressed, due to steric hindrance caused by the structure of the side chain of the second structural unit. Also, nucleophilicity or electrophilicity of the second reactive functional group may be reduced, due to other atom linked to the side chain of the second structural unit.

As the second structural unit, a structural unit derived from an ethylenically unsaturated monomer having no reactive functional group or having a second reactive functional group is preferred. Herein, the ethylenically unsaturated monomer refers to a monomer having an ethylenically unsaturated bond such as a vinyl group, an allyl group, a (meth)acryloxy group, or a (meth)acrylamide group.

Examples of the second structural unit include a structural unit derived from a (meth)acrylate monomer having no reactive functional group or having a second reactive functional group, a structural unit derived from a (meth)acrylamide monomer having no reactive functional group or having a second reactive functional group, and a structural unit derived from a styrene monomer having no reactive functional group or having a second reactive functional group. Among them, a structural unit derived from a (meth) acrylate monomer having no reactive functional group or having a second reactive functional group and a structural unit derived from a (meth)acrylamide monomer having no reactive functional group or having a second reactive functional group are preferred, from the view point of the suppression of nonspecific adsorption.

As the second structural unit, a structural unit having a hydrophilic group is preferred, and a structural unit having a hydrophilic group on a side chain is more preferred. The number of the hydrophilic group is preferably 1 to 3 and more preferably 1 per the above structural unit.

Herein, hydrophilicity means to have a strong affinity for water.

The hydrophilic group may be charged under aqueous neutral conditions, and may not be charged under the same conditions.

The hydrophilic group that is charged under aqueous neutral conditions includes basic groups such as quaternary ammonium groups (e.g., trimethylammonium chloride group); acid groups such as phosphate groups and sulfo groups; and groups having a zwitterionic structure. When the second structural unit has a hydrophilic group that is charged under aqueous neutral conditions as above, a salt may be formed, and the hydrophilic group may have a counter ion.

The hydrophilic group that is not charged under aqueous neutral conditions includes a hydroxy group, an alkoxy group, a polyoxyalkylene group, a sulfonyl group, a sulfinyl group, and a tertiary amino group. The alkoxy group is preferably an alkoxy group having 1 or 2 carbon atoms. Examples include a methoxy group and an ethoxy group.

As the above polyoxyalkylene group, a group represented by $-(R^cO)_q-$ ($R^c$ represents an alkanediyl group and q represents an integer from 2 to 100, and q groups of $R^c$s may be the same or different) is preferred.

The number of carbon atoms in an alkanediyl group represented by $R^c$ is preferably from 2 to 4, more preferably 2 or 3, and especially preferably 2.

In addition, the alkanediyl group represented by $R^c$ may be a straight chain or a branched chain, and specific examples thereof include an ethane-1,2-diyl group, a propane-1,2-diyl group, a propane-1,3-diyl group, and a propane-2,2-diyl group. Among these groups, an ethane-1,2-diyl group is preferred.

q represents an integer from 2 to 100, and is preferably an integer from 3 to 80, more preferably an integer from 4 to 60, further preferably an integer from 5 to 40, further preferably an integer from 6 to 30, and especially preferably and an integer from 7 to 20.

The second structural unit may have one kind of the above hydrophilic groups, or may have two or more kinds thereof.

Among these groups, the hydrophilic group is preferably a hydroxy group, a group having a zwitterionic structure, a polyoxyalkylene group or a phosphate group, more preferably a hydroxy group, a group having a zwitterionic structure or a polyoxyalkylene group, further preferably a hydroxy group or a group having a zwitterionic structure, and especially preferably a group having a zwitterionic structure, from the view point of the suppression of nonspecific adsorption. When the hydrophilic group is a group having a zwitterionic structure, nonspecific adsorption is efficiently suppressed, even when the content ratio (a/b) exceeds 0.3.

As the above group having a zwitterionic structure, an organic group having a quaternary ammonium salt cationic functional group and a monovalent or divalent anionic functional group selected from the group consisting of $-(C=O)O^-$, $-SO_3^-$ and $-O-(O=P-O^-)-O-$ is preferred, an organic group represented by the following formula (3) or (4) is more preferred, and an organic group represented by the following formula (3) is especially preferred, from the view point of the suppression of nonspecific adsorption.

(3)

wherein $R^6$ and $R^7$ independently represent a single bond or a divalent organic group having 1 to 10 carbon atoms, $R^8$ represents $-(C=O)O^-$ or $-SO_3^-$, and $R^9$ and $R^{10}$ independently represent a methyl group or an ethyl group.

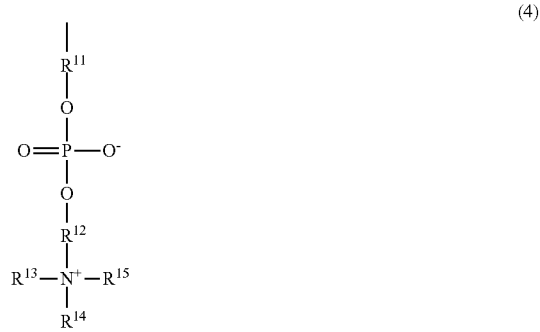

(4)

wherein $R^{11}$ and $R^{12}$ independently represent a single bond or a divalent organic group having 1 to 10 carbon atoms, and $R^{13}$, $R^{14}$ and $R^{15}$ independently represent a methyl group or an ethyl group.

$R^6$ and $R^7$ in the formula (3) and $R^{11}$ and $R^{12}$ in the formula (4) independently represent a single bond or a divalent organic group having 1 to 10 carbon atoms, and is preferably a divalent organic group having 1 to 10 carbon atoms, more preferably a divalent hydrocarbon group having 1 to 10 carbon atoms, or a group having one or more selected from an ether bond, an amide bond and an ester bond between carbon-carbon atoms in a divalent hydrocarbon group having 2 to 10 carbon atoms, and especially preferably a divalent hydrocarbon group having 1 to 10 carbon atoms, from the view point of the suppression of nonspecific adsorption.

When the divalent organic group is a divalent hydrocarbon group, the number of carbon atoms is preferably from 1 to 8, more preferably from 1 to 6, further more preferably from 1 to 4, and especially preferably from 1 to 3. Meanwhile, when the divalent organic group is a group having one or more selected from an ether bond, an amide bond and an ester bond between carbon-carbon atoms in a divalent hydrocarbon group, the number of carbon atoms of the divalent hydrocarbon group in such a group is preferably from 2 to 8, more preferably from 2 to 6, further preferably from 2 to 4, and especially preferably from 2 or 3.

As the "divalent hydrocarbon group" in $R^6$, $R^7$, $R^{11}$ and $R^{12}$, a divalent aliphatic hydrocarbon group is preferred. The divalent aliphatic hydrocarbon group may be a straight chain or a branched chain.

As the above divalent aliphatic hydrocarbon group, an alkanediyl group is preferred, and specific examples thereof include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, and a hexane-1,6-diyl group.

$R^8$ in the formula (3) is preferably —(C=O)O−. $R^9$ and $R^{10}$ in the formula (3), and $R^{13}$, $R^{14}$ and $R^{15}$ in the formula (4), are preferably a methyl group.

Also, specific preferred examples of the second structural unit include structural units represented by the following formula (5).

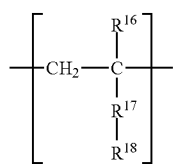

(5)

wherein $R^{16}$ represents a hydrogen atom or a methyl group, $R^{17}$ represents —O—*, —(C=O)—O—*, —(C=O)—NR$^{19}$—* ($R^{19}$ represents a hydrogen atom or an organic group having 1 to 10 carbon atoms, and * represents a position bound to $R^{18}$ in the formula (5)) or a phenylene group, and $R^{18}$ represents a group having a zwitterionic structure, an organic group having a hydroxy group, or an organic group having a polyoxyalkylene group.

In the formula (5), $R^{17}$ is preferably —(C=O)—O—* or —(C=O)—NR$^{19}$—* from the view point of the suppression of nonspecific adsorption.

$R^{19}$ represents a hydrogen atom or an organic group having 1 to 10 carbon atoms.

The number of carbon atoms of the organic group represented by $R^{19}$ is preferably from 1 to 8, more preferably from 1 to 6, and especially preferably from 1 to 3. Also, the organic group is preferably a hydrocarbon group, and more preferably an aliphatic hydrocarbon group. The aliphatic hydrocarbon group may be a straight chain or a branched chain, and specific examples thereof include alkyl groups such as a methyl group, an ethyl group, an n-propyl group, an isopropyl group, an n-butyl group, an isobutyl group, a sec-butyl group, a tert-butyl group, a pentyl group, a hexyl group, a heptyl group, and an octyl group.

Among $R^{19}$s as above, a hydrogen atom is preferred.

The group having a zwitterionic structure represented by $R^{18}$ is the same as the group having a zwitterionic structure.

Examples of the organic group having a hydroxy group represented by $R^{18}$ include groups represented by the following formula (6).

*—$R^{20}$—OH (6)

wherein $R^{20}$ represents a divalent organic group, and * represents a position bound to $R^{17}$ in the formula (5).

The divalent organic group represented by $R^{20}$ includes divalent hydrocarbon groups, and groups having one or more selected from an ether bond, an amide bond and an ester bond between carbon-carbon atoms in a divalent hydrocarbon group having 2 or more carbon atoms, and is preferably a divalent hydrocarbon group.

When the divalent organic group is a divalent hydrocarbon group, the number of carbon atoms is preferably from 1 to 8, more preferably from 1 to 6, further more preferably from 1 to 4, and especially preferably from 1 to 3. Meanwhile, when the divalent organic group is a group having one or more selected from an ether bond, an amide bond and an ester bond between carbon-carbon atoms in a divalent hydrocarbon group having 2 or more carbon atoms, the number of carbon atoms of the divalent hydrocarbon group in such a group is preferably from 2 to 8, more preferably from 2 to 6, further preferably from 2 to 4, and especially preferably from 2 or 3.

As the "divalent hydrocarbon group" in $R^{20}$, a divalent aliphatic hydrocarbon group is preferred. The divalent aliphatic hydrocarbon group may be a straight chain or a branched chain.

As the above divalent aliphatic hydrocarbon group, an alkanediyl group is preferred, and specific examples thereof include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, and a hexane-1,6-diyl group.

As the organic group having a polyoxyalkylene group represented by $R^{18}$, a group represented by —(R$^c$O)$_q$—R$^d$ is preferred (R$^d$ represents an alkyl group having 1 to 4 carbon atoms. R$^c$ and q are each the same as above, R$^c$ represents an alkanediyl group, and q represents an integer from 2 to 100).

The number of carbon atoms in an alkyl group represented by R$^d$ is preferably from 1 to 3, and more preferably 1 or 2. Also, the alkyl group represented by R$^d$ may be a straight chain or a branched chain, and specific examples thereof include a methyl group, an ethyl group, an n-propyl group, an isopropyl group, an n-butyl group, an isobutyl group, a sec-butyl group, and a tert-butyl group, and a methyl group is especially preferred.

The content of the second structural unit is preferably 30 to 99% by mass, more preferably 35 to 95% by mass, and especially preferably 65 to 95% by mass, based on the entire amount of the random polymer structure.

The content of the second structural unit may be measured by using, for example, NMR.

The random polymer structure may have a structural unit other than the first structural unit and the second structural unit. Also, the chain polymer bound to the solid-phase carrier of the present invention may have a polymer structure other than the random polymer structure. Examples of the chain polymer include, other than the random polymer represented by -(first structural unit)-ran-(second structural unit)-, a polymer represented by -(other polymer structure)-(first structural unit)-ran-(second structural unit)-, and a polymer represented by -(first structural unit)-ran-(second structural unit)-(other polymer structure)-( represents a binding position on the surface side of the solid-phase carrier, and ran means that two structural units adjacent thereto are a random polymer structure). Among these polymers, the random polymer represented by -(first structural unit)-ran-(second structural unit)- and a polymer represented by -(other polymer structure)-(first structural unit)-ran-(second structural unit)- are preferred.

Also, as the other polymer structure, a block polymer structure constituted by the second structural unit is preferred.

In addition, the chain polymer is preferably a chain polymer formed by polymerization of an ethylenically unsaturated bond, and more preferably a chain vinyl polymer.

Also, one end of the chain polymer may directly bind or bind via a linking group as long as it binds to the solid-phase carrier, and it is preferred that one end bind to the solid-phase carrier via a divalent linking group. The divalent linking group is covalently bonded to the surface of the solid-phase carrier, and is also covalently bonded to the chain polymer. It is preferred that the divalent linking group bind to the surface of the solid-phase carrier via an ester bond or amide bond, and more preferred that the divalent linking group binds to the surface of the solid-phase carrier via an ester bond, in that the binding is stable and easily selectively cut by hydrolysis.

Also, the divalent linking group is preferably a divalent linking group containing a residual group of a polymerization initiating group. As the polymerization initiating group, a polymerization initiating group capable of living polymerization is preferred, a living radical polymerization initiating group is more preferred, an atom transfer radical polymerization initiating group, a reversible addition-fragmentation chain transfer polymerization initiating group, and a polymerization initiating group of radical polymerization via nitroxide are further preferred, and an atom transfer radical polymerization initiating group is especially preferred. Examples of the divalent linking group containing a residual group of an atom transfer radical polymerization initiating group include a divalent group represented by the following formula (7-1) or (7-2).

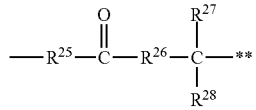

(7-1)

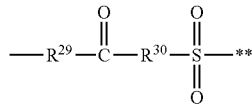

(7-2)

wherein $R^{25}$ and $R^{29}$ represent —O—, —S— or —$N^{31}$— ($R^{31}$ represents a hydrogen atom or an alkyl group having 1 to 3 carbon atoms), $R^{26}$ and $R^{30}$ independently represent a single bond or a phenylene group, $R^{27}$ and $R^{28}$ independently represent a hydrogen atom, an alkyl group or an aryl group, and ** represents a position bound to the end of a chain polymer.

$R^{25}$ and $R^{29}$ are preferably —O—, in that the binding is stable and easily selectively cut by hydrolysis. Also, examples of the alkyl group represented by $R^{31}$ include a methyl group, an ethyl group, an n-propyl group, and an isopropyl group.

Moreover, $R^{26}$ and $R^{30}$ are preferably a single bond, and $R^{27}$ and $R^{28}$ are preferably an alkyl group.

The number of carbon atoms in the alkyl group represented by $R^{27}$ and $R^{28}$ is preferably from 1 to 8, more preferably from 1 to 4, and especially preferably 1 or 2. The alkyl group may be a straight chain or a branched chain, and specific examples thereof include a methyl group, an ethyl group, an n-propyl group, an isopropyl group, an n-butyl group, an isobutyl group, a sec-butyl group, a tert-butyl group, a pentyl group, a hexyl group, a heptyl group, and an octyl group.

The number of carbon atoms in the aryl group represented by $R^{27}$ and $R^{28}$ is preferably from 6 to 12. Specific preferred examples of the aryl group include a phenyl group.

Meanwhile, the other end of a chain polymer is not particularly limited, and a halogen atom is preferred. Examples of the halogen atom include a bromine atom, a chlorine atom, and a fluorine atom.

Also, in the solid-phase carrier of the present invention, the content ratio of the number of moles "a" of the first reactive functional group to the number of moles "b" of the entire structural unit contained in the chain polymer, (a/b), is from 0.01 to 0.7. By such a constitution, nonspecific adsorption is suppressed.

The content ratio (a/b) is preferably 0.025 or more, and more preferably 0.05 or more, from the view point of allowing a ligand to easily bind, and is also preferably 0.6 or less, more preferably 0.4 or less, further preferably 0.35 or less, and especially preferably 0.25 or less, from the view point of the suppression of nonspecific adsorption.

Also, when the chain polymer has a hydrophilic group, the content ratio of the number of moles "c" of the hydrophilic group contained in the chain polymer to the number of moles "b" of the entire structural unit contained in the chain polymer, (c/b), is preferably 0.3 or more, more preferably 0.4 or more, further preferably 0.6 or more, and especially preferably 0.75 or more, from the view point of allowing a ligand to easily bind, and also preferably 0.99 or less, more preferably 0.95 or less, and especially preferably 0.9 or less, from the view point of easy polymer synthesis.

The numbers of moles "a" to "c" each represent the number of moles contained in one chain polymer, and can be calculated by X-ray photoelectron spectroscopy, NMR analysis of the chain polymer, or from, for example, the weight of the chain polymer binding to 1 g of a solid-phase carrier, the molecular weight of the chain polymer and the amount of reactive functional group. Specifically, it can be measured in accordance with a method described in the examples mentioned below.

As the solid-phase carrier of the present invention, one formed by binding the chain polymer at least to the surface of the solid-phase carrier is preferred.

In addition, it is preferred that the chain polymer form a polymer brush on the surface of the solid-phase carrier. The density of the above chain polymer occupying the surface of the solid-phase carrier of the present invention is preferably 0.1 polymers/$nm^2$ or more, more preferably 0.3 polymers/$nm^2$ or more, and further preferably 0.5 polymers/$nm^2$ or more, from the view point of suppressing nonspecific adsorption, from the view point of the amount of bound ligand and from the view point of satisfying both an increase in sensitivity and a decrease in noise in detection, and also preferably 2 polymers/$nm^2$ or less, more preferably 1.5 polymers/$nm^2$ or less, further preferably 1.3 polymers/$nm^2$ or less, and especially preferably 1.2 polymers/$nm^2$ or less, from the view point of easily forming the polymer brush.

The density of the above chain polymer can be calculated, for example, by the following formula. Specifically, chain polymers are released from a solid-phase carrier by, for example, hydrolysis, and the density can be measured in accordance with a method described in the examples mentioned below.

Density of chain polymer (chain polymers/nm$^2$)=Number of chain polymers binding to 1 g of carrier (chain polymers)/ Total surface area of 1 g of carrier (nm$^2$)

Also, the total surface area of 1 g of carrier means a total surface area of the carrier before binding of the chain polymer.

Moreover, the number average molecular weight (Mn) of the chain polymer is preferably from 1,000 to 100,000, more preferably from 3,000 to 50,000, and further more preferably from 5,000 to 30,000, from the view point of the suppression of nonspecific adsorption.

Also, the weight average molecular weight (Mw) of chain polymer is preferably from 1,000 to 100,000, and more preferably from 3,000 to 50,000, from the view point of the suppression of nonspecific adsorption.

In addition, the molecular weight distribution (Mw/Mn) is preferably from 1.0 to 2.5, more preferably from 1.0 to 2.0, further preferably from 1.0 to 1.8, and further preferably from 1.0 to 1.5, from the view point of the suppression of nonspecific adsorption and increasing the activity of a ligand bound to a solid-phase carrier.

The number average molecular weight and the weight average molecular weight mean average molecular weights in terms of polyethylene glycol, which are measured by gel permeation chromatography after releasing chain polymers from a solid-phase carrier by, for example, hydrolysis. The molecular weight of the chain polymer before a reactive functional group is introduced is measured by a method as described in the examples mentioned below, and the number average molecular weight and the weight average molecular weight can also be calculated from such a molecular weight, the number of moles of a structural unit into which a reactive functional group is introduced, and the structure of a compound used for introducing a reactive functional group.

The portions other than a chain polymer (supporting body portion, support part) constituting the solid-phase carrier of the present invention may be organic substances or inorganic substances such as metals or metal oxides, but not particularly limited thereto. It is preferred that the solid-phase carrier of the present invention contain a resin in addition to a chain polymer. Whereby, the chain polymer can be easily introduced.

As the resin, naturally-occurring polymers constituted of polysaccharides such as agarose, dextran and cellulose, or synthetic polymers may be used.

In addition, a form of the solid-phase carrier of the present invention is not particularly limited and may be any of, for example, particles, monoliths, films, fibers and plates, and particles are preferred and magnetic particles are more preferred, from the view point of ease in detection or separation of a target substance. In the case of employing the form of particles, the polymer density of the chain polymer can also be increased. Also, the method for producing magnetic particles is described in JP 2007-224213 A in detail.

In the present description, the "magnetic particles" means particles with a magnetic substance. The solid-phase carrier of the present invention has high water dispersibility even in the form of magnetic particles. Also, in the case of magnetic particles, the particles can be separated by using, for example, a magnet without using, for example, a centrifuge, and thus the solid-phase carrier can be simply or automatically separated from a sample.

Moreover, the magnetic substance may have any of ferromagnetism, paramagnetism and superparamagnetism, and is preferably superparamagnetic, from the view point of easing separation in a magnetic field and redispersion after removing the magnetic field. Examples of the magnetic substance include metals such as ferrite, iron oxide, iron, manganese oxide, manganese, nickel oxide, nickel, cobalt oxide and cobalt, or alloys.

Also, specific examples of the magnetic particles include those formed by binding the above chain polymer at least to the surface of any particles in the following (i) to (iv). Porous or non-porous magnetic polymer particles are preferred.

(i) Particles in which magnetic fine particles are dispersed in a continuous phase including a non-magnetic substance such as a resin (ii) Particles in which a secondary agglomerate of magnetic fine particles is constituted as a core and a non-magnetic substance such as a resin is constituted as a shell (iii) Particles in which mother particles having core particles constituted from a non-magnetic substance such as a resin and a magnetic layer (secondary agglomerate layer) including magnetic fine particles provided to the surface of the core particles are constituted as a core, and a non-magnetic layer such as a resin is provided to the outermost layer of the mother particles as a shell (hereinafter, referred to as the outermost layer shell)

(iv) Particles in which magnetic fine particles are dispersed in the holes of porous particles including, for example, a resin and silica, in which a non-magnetic layer such as a resin may be provided to the outermost layer of particles as a shell The particles of (i) to (iv) are all known and can be produced in accordance with a conventional method.

Examples of the resins in the core particles in (iii) above and the porous particles in (iv) above include resins derived from one or two or more monomers selected from monofunctional monomers and polyfunctional monomers.

Examples of the above monofunctional monomer include monofunctional aromatic vinyl monomers such as styrene, α-methylstyrene and halogenated styrene; and monofunctional (meth)acrylate monomers such as methyl (meth)acrylate, ethyl (meth)acrylate, stearyl (meth)acrylate, cyclohexyl (meth)acrylate and isobornyl (meth)acrylate.

Examples of the above polyfunctional monomer include polyfunctional aromatic vinyl monomers such as divinylbenzene; polyfunctional (meth)acrylate monomers such as ethyleneglycol di(meth)acrylate, trimethylolpropane tri (meth)acrylate, dipentaerythritol hexa(meth)acrylate and allyl (meth)acrylate; and conjugated diolefins such as butadiene and isoprene.

In addition, as the resins in (i) and (ii) above as well as the resins in the outermost layer shell in (iii) and (iv) above, a resin having one or two or more functional groups selected from the group consisting of a glycidyl group, an amino group and a hydroxy group at least on the surface is preferred. The above functional groups may be introduced by the chemical modification of the resin surface, or by polymerization of a monomer composition at least containing one or two or more monomers having the above functional group. Examples of the above chemical modification include the production of a hydroxy group by hydrolysis of a glycidyl group, and the production of an amino group by reduction of a nitro group. As the above monomer composition having a functional group, a monomer composition at least containing a glycidyl group-containing monomer is more preferred (hereinafter, particles in which the resin in the above outermost layer shell is a resin formed by a monomer composition at least containing a glycidyl group-containing monomer are also referred to as a glycidyl group-containing magnetic particles). One or two or more monomers selected from the above monofunctional monomers and polyfunctional monomers may be further contained.

Examples of the glycidyl group-containing monomer include glycidyl (meth)acrylate and allyl glycidyl ether. Examples of the amino group-containing monomer include 2-aminoethyl (meth)acrylate. Examples of the hydroxy group-containing monomer include 1,4-cyclohexane dimethanol mono(meth)acrylate.

In addition, when the solid-phase carrier of the present invention is a particle, the average particle diameter (volume average particle diameter) is preferably from 0.1 to 500 μm, more preferably from 0.2 to 50 μm, and further preferably from 0.3 to 10 μm. Within such a range, when the solid-phase carrier is a magnetic particle, the magnetic collection speed becomes faster and handling properties are improved, and also the amount of bound ligand becomes larger, and for example, detection sensitivity becomes higher. In addition, the coefficient of variation of the average particle diameter is only required to be about 20% or less.

The specific surface area is only required to be about from 1.0 to 2.0 $m^2/g$.

The above average particle diameter and specific surface area can be measured by, for example, laser diffraction scattering particle size distribution measurement.

Figure 2:
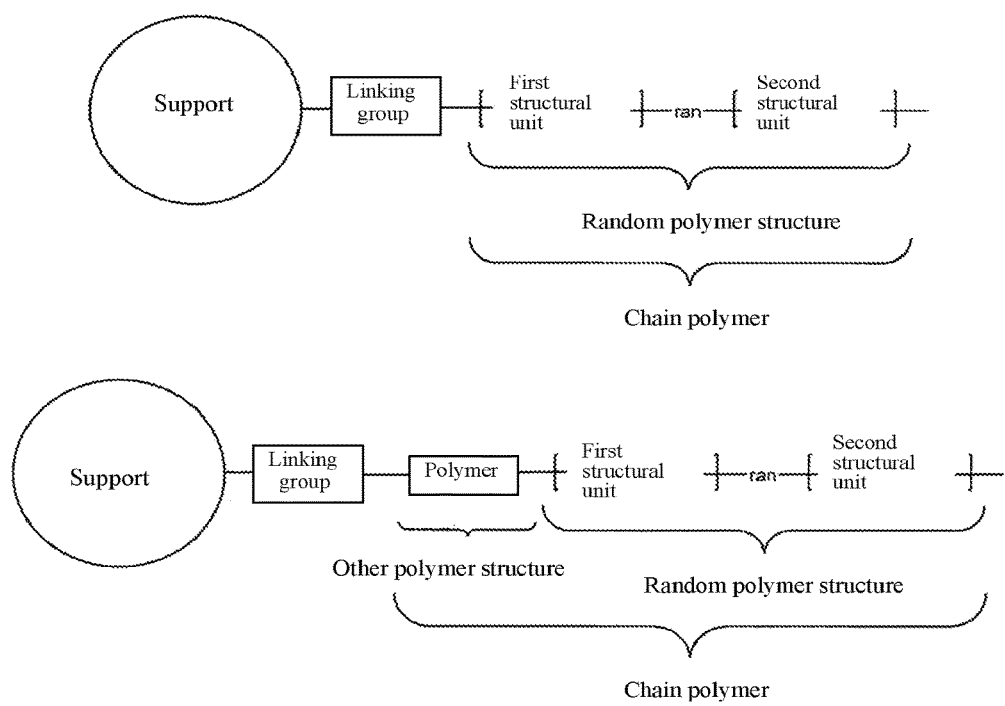
FIG. 2 shows schematic views of examples of the solid-phase carrier.

In addition, the solid-phase carrier of the present invention can be, for example, schematically shown in FIG. 2 (ran means that two structural units adjacent thereto are a random polymer structure).

<Method for Producing Solid-Phase Support>

The solid-phase carrier of the present invention can be produced by properly combining conventional methods. As the method for producing the solid-phase carrier of the present invention, a method including the following Step 1 and Step 2 is preferred, for example, from the view point of increasing the density of the chain polymer occupying the surface of the solid-phase carrier and further suppressing nonspecific adsorption, from the view point of binding the chain polymer having a narrow molecular weight distribution to the solid-phase carrier and further suppressing nonspecific adsorption, and from the view point of enhancing function of the ligand bound to the solid-phase carrier.

(Step 1) a step of preparing a carrier having a polymerization initiating group (hereinbelow, also referred to as a polymerization initiating group-containing carrier) at least on the surface (Step 2) a step of forming, from the polymerization initiating group as a starting point, a chain polymer including a random polymer structure containing a first structural unit having a reactive functional group, and a second structural unit having no reactive functional group or having a reactive functional group having a reactivity lower than that of the reactive functional group of the first structural unit, such that the content ratio of the number of moles "a" of the reactive functional group contained in the first structural unit to the number of moles "b" of the entire structural unit contained in the chain polymer, (a/b), is from 0.01 to 0.7

Specific examples of the above production method include the following methods <PR-1> to <PR-3>. Here, when other polymer structure such as a block polymer structure constituted by the second structural unit is introduced to a chain polymer, the method of introducing this polymer structure may be performed before and/or after Step 2, in accordance with a conventional method.

<PR-1> A method including (Step 1) of preparing a polymerization initiating group-containing carrier, (Step 2-1-1) of polymerizing a monomer inducing a second structural unit, from the polymerization initiating group as a starting point, to form a polymer, and (Step 2-1-2) of randomly introducing a first reactive functional group into a part of the side chain of the second structural unit constituting the polymer obtained in the step to form a first structural unit having the first reactive functional group.

<PR-2> A method including (Step 1) of preparing a polymerization initiating group-containing carrier, and (Step 2-2) of random-copolymerizing a monomer inducing a first structural unit and a monomer inducing a second structural unit, from the polymerization initiating group as the starting point.

<PR-3> A method including (Step 1) of preparing a polymerization initiating group-containing carrier, (Step 2-3-1) of randomly copolymerizing a monomer having a hydroxy group or amino group and a monomer having no hydroxy group and amino group, from the polymerization initiating group as the starting point, to form a random polymer structure, and (Step 2-3-2) of introducing a first reactive functional group into the structural unit having a hydroxy group or amino group in the random polymer structure obtained in the step to form a first structural unit having the first reactive functional group.

These methods will be described with reference to a method for producing a solid-phase carrier to which a chain polymer having a carboxy group, an amino group or a tosyl group as the first reactive functional group is bound as an example.

(Step 1)

A polymerization initiating group-containing carrier can be obtained, for example, by bringing a compound having a polymerization initiating group into contact with a carrier material having one or two or more groups selected from a hydroxy group, an amino group, an epoxy group and a carboxy group (hereinafter, these are collectively referred to as hydroxy group or the like) at least on the surface (hereinafter, also referred to as a carrier material) to convert a hydrogen atom contained in the above hydroxy group, etc. into the polymerization initiating group (hereinafter, this reaction is also referred to as a polymerization initiating group introducing reaction). Among the above carrier materials, a carrier material having a hydroxy group at least on the surface can be obtained, for example, by bringing the above glycidyl group-containing magnetic particles into contact with an acid such as inorganic acid or an organic acid to conduct ring opening of the glycidyl group.

Also, a polymerization initiating group-containing carrier can also be obtained by polymerizing a monomer composition containing a monomer having a polymerization initiating group. Examples of the monomer having a polymerization initiating group include 2-(2-bromoisobutyryloxy) ethyl methacrylate.

As the above compound having a polymerization initiating group, a compound having a polymerization initiating group capable of living polymerization is preferred, a compound having a living radical polymerization initiating group is more preferred, a compound having an atom transfer radical polymerization initiating group, a compound having a reversible addition-fragmentation chain transfer polymerization initiating group and a compound having a polymerization initiating group of radical polymerization via nitroxide are further preferred, and a compound having an atom transfer radical polymerization initiating group is especially preferred. Examples of the compound having an atom transfer radical polymerization initiating group include 2-bromoisobutyryl bromide, 4-(bromomethyl)benzoic acid, ethyl 2-bromoisobutyrate, 2-bromopropionyl bromide and tosyl chloride.

In the polymerization initiating group introducing reaction, a total amount of compound having a polymerization initiating group used is normally about from 0.001 to 100 times by mass and preferably about from 0.01 to 50 times by mass, with respect to a carrier material.

It is preferred that the polymerization initiating group introducing reaction be carried out in the presence of a basic catalyst such as triethylamine, N,N-dimethyl-4-aminopyridine, diisopropylethylamine or pyridine. One of these basic catalysts may be used alone or two or more of these basic catalysts may be used in combination.

The total amount of basic catalyst used is normally about from 1 to 10 molar equivalents and preferably about from 1 to 5 molar equivalents, with respect to a compound having a polymerization initiating group.

It is also preferred that the polymerization initiating group introducing reaction be carried out in the presence of a solvent. Examples of solvents include ether solvents such as tetrahydrofuran, 1,4-dioxane and 1,3-dioxane; and protic solvents such as dimethylformamide and dimethylsulfoxide, and one of these solvents can be used alone, or two or more of these solvents can be used in combination.

In addition, the reaction time of the polymerization initiating group introducing reaction is normally about from 30 minutes to 24 hours, and the reaction temperature may be properly selected from the boiling point of a solvent or lower.

(Step 2-1-1, Step 2-2 and Step 2-3-1)

Step 2-1-1 is a step of polymerizing a monomer inducing a second structural unit (hereinafter, also referred to as monomer (11)), from the polymerization initiating group as a starting point, to form a polymer.

Step 2-2 is a step of randomly copolymerizing a monomer inducing a first structural unit (hereinafter, also referred to as monomer (12)) and a monomer inducing a second structural unit (hereinafter, also referred to as monomer (13)), from the polymerization initiating group as a starting point.

Step 2-3-1 is a step of randomly copolymerizing a monomer having a hydroxy group or amino group (hereinafter, also referred to as monomer (14)) and a monomer having no hydroxy group and amino group (hereinafter, also referred to as monomer (15)), from the polymerization initiating group as a starting point, to form a random polymer structure.

Examples of the monomer (11) used in Step 2-1-1 include monomers inducing a second structural unit having a hydrophilic group capable of introducing a carboxy group, an amino group or a tosyl group (e.g., hydroxy group or the like. The same shall apply hereafter.).

As the monomer (11), a monomer having a hydroxy group is preferred. Examples of the monomer having a hydroxy group are 2-hydroxyethyl (meth)acrylate, 2-hydroxyethyl (meth)acrylamide, 2-hydroxypropyl (meth)acrylate, 2-hydroxypropyl (meth)acrylamide, 2-hydroxybutyl (meth)acrylate, 2-hydroxybutyl (meth)acrylamide, glycerol 1-(meth)acrylate, and glycerol 1-(meth)acrylamide.

One of these monomers may be used alone, or two or more thereof may be used in combination.

Examples of the monomer (12) used in Step 2-2 include monomers having a carboxy group, an amino group or a tosyl group. Examples include (meth)acrylic acid, (meth)acrylic acid salts and aminoethyl (meth)acrylate, and 2-(meth)acryloyloxyethyl succinate. When producing a solid-phase carrier to which a chain polymer having an epoxy group as the first reactive functional group is bound, for example, glycidyl (meth)acrylate may be used.

One of these monomers may be used alone, or two or more thereof may be used in combination.

Examples of the monomer (13) used in Step 2-2 include monomers having hydrophilic groups such as a monomer having a hydroxy group, a monomer having a polyoxyethylene group, a monomer having a group having a zwitterion, a monomer having a phosphate group, a monomer having a quaternary ammonium group, and further, monomers having hydrophilicity such as dimethyl (meth)acrylamide, dimethylaminopropyl (meth)acrylamide, isopropyl (meth)acrylamide and diethyl (meth)acrylamide.

The monomer having a hydroxy group includes the same ones as in the monomer (11). Examples of the monomer having a polyoxyethylene group are methoxypolyethylene glycol mono(meth)acrylate and methoxypolyethylene glycol mono(meth)acrylamide. Examples of the monomer having a group having a zwitterion are

[2-((meth)acryloyloxy)ethyl](carboxylatomethyl)dimethylaminium,

[2-((meth)acryloyloxy)ethyl](carboxylatoethyl)dimethylaminium,

[2-((meth)acryloyloxy)ethyl](carboxylatopropyl)dimethylaminium,

[2-((meth)acryloyloxy)ethyl]dimethyl-(3-sulfomethyl)ammonium hydroxide,

[2-((meth)acryloyloxy)ethyl]dimethyl-(3-sulfoethyl)ammonium hydroxide,

[2-((meth)acryloyloxy)ethyl]dimethyl-(3-sulfopropyl)ammonium hydroxide, and

O-[2-((meth)acryloyloxy)ethoxy(oxylato)phosphinyl]choline

Examples of the monomer having a phosphate group are 2-phosphoric ethyl (meth)acrylate and 2-phosphoric ethyl (meth)acrylamide. Examples of the monomer having a quaternary ammonium group are.

One of these monomers may be used alone, or two or more thereof may be used in combination.

The monomer (14) used in Step 2-3-1 is a monomer having a hydroxy group or an amino group. The monomer having a hydroxy group includes the same ones as in the monomer (11). Examples of the monomer having an amino group include aminoethyl (meth)acrylate.

One of these monomers may be used alone, or two or more thereof may be used in combination.

The monomer (15) used in Step 2-3-1 is a monomer having no hydroxy group and amino group. Specifically, it is a monomer having a hydrophilic group other than a hydroxy group and an amino group. Examples are a monomer having a polyoxyethylene group, a monomer having a group having a zwitterion, and a monomer having a phosphate group. The monomer having a polyoxyethylene group, the monomer having a group having a zwitterion and the monomer having a phosphate group include the same ones as in the monomer (13).

One of these monomers may be used alone, or two or more thereof may be used in combination.

The amounts of the monomers (11) to (15) used are each normally about from 5 to 10,000 molar equivalents and preferably about from 10 to 5,000 molar equivalents, with respect to a polymerization initiating group binding to the surface of a carrier.

The polymerization method for the polymerization reaction in the step 2-1-1, the step 2-2 and the step 2-3-1 may be selected depending on the kind of polymerization initiating group, and living polymerization is preferred, living radical polymerization is more preferred, atom transfer radical polymerization (ATRP polymerization), reversible addition-fragmentation chain transfer polymerization (RAFT polymerization) and radical polymerization via nitroxide (NMP) are further preferred, and atom transfer radical polymerization is especially preferred, from the view point of simply and easily obtaining a target product. By polymerization by atom transfer radical polymerization, a chain polymer can be allowed to simply bind to a wide variety of carriers. Furthermore, biocompatibility, high compressive elasticity, low frictional characteristics and size exclusion characteristics are imparted to a solid-phase carrier thus obtained, and the density of chain polymer occupying the surface of a solid-phase carrier is increased, and thus nonspecific adsorption is suppressed.

Also, when the polymerization reaction in the step 2-1-1, the step 2-2 and the step 2-3-1 is carried out by atom transfer radical polymerization, it is preferred that the reaction be carried out in the presence of a transition metal compound and a ligand, from the view point of reaction efficiency.

As the transition metal compound, a copper compound is preferred. Examples of the copper compound include halogenated copper such as copper(I) bromide, copper(II) bromide, copper(I) chloride and copper(II) chloride, and further, copper(I) triflate and copper(II) triflate. One of these compounds may be used alone, or two or thereof may be used in combination. The total amount of transition metal compound used is normally about from 1 to 10,000 ppm in the reaction system.

As the ligand, a ligand including two or more nitrogen atoms in the same molecule is preferred. Examples of the ligand including two or more nitrogen atoms in the same molecule include tris(2-pyridylmethyl)amine, bipyridine, bipyridine derivatives, and tris [2-(dimethylamino)ethyl] amine. One of these ligands may be used alone, or two or more thereof may be used in combination. The total amount of ligand used is normally about from 0.5 to 10 molar equivalents with respect to a transition metal compound.

It is also preferred that the polymerization reaction in the step 2-1-1, the step 2-2 and the step 2-3-1 be carried out in the presence of a reducing agent and a solvent, from the view point of reaction efficiency.

Examples of the reducing agent include ascorbic acid, glucose, hydrazine and copper, and one of these reducing agents can be used alone, or two or more thereof can be used in combination.

Examples of the solvent include aqueous solvents and organic solvents. Specific examples include water; amide solvents such as dimethylformamide; alcohol solvents such as methanol and ethanol; and ether solvents such as anisole, and one of these solvents can be used alone, or two or more thereof can be used in combination. Particularly, the polymerization reaction is preferably carried out in an aqueous solvent. The aqueous solvent is simple to handle and easy to prepare the reaction system. When atom transfer radical polymerization is carried out in an aqueous solvent, it is preferred that the aqueous solvent be a buffer. The preferred concentration of the buffer is 10 to 100 mM.

Also, the pH in the reaction system of the polymerization reaction is preferably from 3 to 10, and more preferably from 7 to 9. The reaction time of the polymerization reaction is normally about from 30 minutes to 12 hours, and the reaction temperature may be properly selected from the boiling point of a solvent or lower. The polymerization reaction proceeds even under mild conditions of about from 25 to 60° C.

(Step 2-1-2 and Step 2-3-2)

The step 2-1-2 is a step of randomly introducing a first reactive functional group into a part of the side chain of the second structural unit constituting the polymer obtained in the step 2-1-1 by an addition reaction, a substitution reaction, a condensation reaction or a deprotection reaction to form a first structural unit having the first reactive functional group. Whereby, a part of the second structural unit is converted to the first structural unit, thus a random polymer structure of the first structural unit and the second structural unit is obtained.

The step 2-3-2 is a step of introducing a first reactive functional group into the structural unit having a hydroxy group or amino group in the random polymer structure obtained in the step 2-3-1 by an addition reaction, a substitution reaction, a condensation reaction or a deprotection reaction to form a first structural unit having the first reactive functional group. Whereby, the structural unit having a hydroxy group or amino group is converted to the first structural unit, thus a random polymer structure of the first structural unit and the second structural unit is obtained.

Examples of methods for introducing a carboxy group include a method in which a hydroxy group or amino group derived from the monomer (11) or (14) is subjected to an addition reaction with carboxylic anhydride.

Examples of the carboxylic anhydride include succinic anhydride, maleic anhydride, glutaric anhydride, phthalic anhydride, and hexahydrophthalic anhydride. Among them, succinic anhydride is preferred, from the view point of easy progression of the reaction with a hydroxy group or amino group.

The total amount of, for example, carboxylic anhydride used is normally about from 0.01 to 0.99 molar equivalents with respect to a structural unit derived from the monomer (11), and is normally about from 1 to 100 molar equivalents with respect to a structural unit derived from the monomer (14).

It is also preferred that the step 2-1-2 and the step 2-3-2 be carried out in the presence of the basic catalyst and solvent that are the same as in the step 1. The reaction time of the step 2-1-2 and the step 2-3-2 is normally about from 30 minutes to 24 hours, and the reaction temperature may be properly selected from the boiling point of a solvent or lower.

The method of forming a chain polymer and the method of introducing a carboxy group, an amino group or a tosyl group are not limited to the above methods. For example, in the step 2-1-2, a molecule (e.g., succinyl dichloride) having a precursor (e.g., acid chloride) of a reactive functional group is first randomly introducing into the side chain of the second structural unit, and then this precursor may be converted to a reactive functional group (e.g., carboxy group). Also, for example, in the steps 2-3-1 to 2-3-2 of PR-3, a polymer is formed by polymerizing a functional group that produces a reactive functional group by hydrolysis (e.g., ester group) and a monomer having a hydrophilic group (e.g., hydroxy group) (e.g., 2-hydroxyethyl methacrylate), and then a reactive functional group (e.g., carboxy group) may be randomly introduced into a part of the side chain of the structural unit constituting the polymer, by partially hydrolyzing the functional group.

Moreover, impurities are hard to nonspecifically adsorb to the solid-phase carrier of the present invention obtained as described above. Specifically, impurities are hard to non-specifically adsorb to the reactive functional group used in binding with a ligand. Also, a ligand is easy to bind to the reactive functional group.

Therefore, the solid-phase carrier of the present invention is used as an affinity support, whereby it can be widely used, for example, for in vitro diagnoses and research in the biochemical field, including, for example, immunoassay using antigen-antibody reactions such as enzyme immunoassay, radioimmunoassay and chemiluminescence immunoassay, and immunoprecipitation and competitive assay; the detection of, for example, proteins and nucleic acids; bio-separation of bio-related materials such as cells, proteins and nucleic acids; drug seeking; and biosensors. The solid-phase carrier of the present invention is especially suitable for use for immunoassay or detecting nucleic acids.

<Ligand-Binding Solid-Phase Support>

The ligand-bound solid-phase carrier of the present invention is formed by binding a ligand to the solid-phase carrier of the present invention.

The above ligand is only required to be a molecule which binds to a target substance, and examples thereof include antibodies; antigens (including incomplete antibodies such as hapten); nucleic acids such as DNA and RNA; nucleotides; nucleosides; oligonucleotides; proteins such as Protein A, Protein G, (strept)avidin, enzymes, lectins and lymphokine; peptides such as insulin; amino acids; saccharides or polysaccharides such as heparin and oligosaccharide; glycoproteins; lipids; glycolipids; vitamins such as biotin; drugs; substrates; hormones; neurotransmitters; viruses; and cells.

Among these ligands, antibodies and antigens are preferred, from the view point of obtaining a ligand-bound solid-phase carrier suitable for, for example, diagnostic agents. The antibodies and antigens are only required to bind to a target substance, and examples thereof include antibodies for coagulation fibrinolysis tests such as anti-antiplasmin antibody, anti-D dimer antibody, anti-FDP antibody, anti-tPA antibody, anti-thrombin-antithrombin complex antibody and anti-FPA antibody or antigens thereof; antibodies for tumor tests such as anti-BFP antibody, anti-CEA antibody, anti-AFP antibody, anti-TSH antibody, anti-ferritin antibody and anti-CA19-9 antibody or antigens thereof; antibodies for serum protein tests such as anti-apolipoprotein antibody, anti-β2-microglobulin antibody, anti-α1-microglobulin antibody, anti-immunoglobulin antibody and anti-CRP antibody or antigens thereof; antibodies for endocrine function tests such as anti-HCG antibody or antigens thereof; antibodies for drug analyses such as anti-digoxin antibody and anti-lidocaine antibody or antigens thereof; antigens for infectious disease tests such as HBs antigen, HCV antigen, HIV-1 antigen, HIV-2 antigen, HTLV-1 antigen, *mycoplasma* antigen, *toxoplasma* antigen and streptolysin O antigen or antibodies thereof; and antigens for autoimmune tests such as DNA antigen and heat-denatured human IgG or antibodies thereof. The antibodies may be polyclonal antibodies or monoclonal antibodies.

Also, when detecting a nucleic acid, it is preferred to use oligonucleotide as a ligand.

The ligand-bound solid-phase carrier can be produced by binding a ligand to the reactive functional group contained in the first structural unit of the solid-phase carrier produced in the production method of the solid-phase carrier of the present invention.

The binding of ligands may be carried out in accordance with a conventional method with reference to the description of, for example, JP 2007-224213 A, and is preferably carried out by a covalent binding method. For example, when a reactive functional group is a carboxy group and a ligand has an amino group, binding may be carried out using a dehydration-condensation agent.

The ligand-bound solid-phase carrier of the present invention can be widely used for, for example, in vitro diagnosis and researches in the biochemistry field. The ligand-bound solid-phase carrier of the present invention is especially suitable for use for immunoassay or detecting nucleic acids.

<Method for Detecting or Separating Target Substance>

The method for detecting or separating a target substance in a sample according to the present invention uses the ligand-bound solid-phase carrier of the present invention.

The target substance is not limited as long as it binds with a ligand, and specific examples thereof include antigens; antibodies such as monoclonal antibodies and polyclonal antibodies (including incomplete antibodies such as hapten); cells (normal cells, and cancer cells such as colon cancer cells and circulating cancer cells in blood); nucleic acids such as DNA and RNA; nucleotides; nucleosides; oligonucleotides; proteins such as Protein A, Protein G, (strept)avidin, enzymes, lectins and lymphokine; bio-related materials such as peptides, amino acids, saccharides and polysaccharides (e.g., heparin and oligosaccharide), glycoproteins, lipids, glycolipids, vitamins, hormones, and viruses, and the target substances may be small molecular compounds such as a drug as a target for drug discovery and biotin. The target substance may be labeled by, for example, a fluorescent substance.

The sample is not limited as long as it includes the above target substance or has the possibility of including a target substance, and specific examples include fermentation medium, cell lysates, prokaryotic cells, eukaryotic cells, suspension of virus particles, tissue fluids, body fluids, urine, blood; blood plasma, blood serum, lymph, cell extract, mucus, saliva, feces, physiological secretions, cell secretions, and buffer solutions containing a target substance.

The detection or separation method of the present invention may be carried out in accordance with a conventional method with reference to the description of, for example, JP 2007-224213 A and WO 2011/034115 A, except that the ligand-bound solid-phase carrier of the present invention is used. Examples thereof include a method including a step of bringing the ligand-bound solid-phase carrier of the present invention into contact with a sample containing a target substance by, for example, mixing (contact step), and a step of separating the ligand-bound solid-phase carrier which has grasped the target substance in the contact step from the sample using, for example, a magnet (separation step). After such a separation step, a step of detecting the target substance or a step of dissociating the ligand and the target substance may be included.

EXAMPLES

Hereinbelow, the present invention will be described in detail by way of examples thereof. It should be noted that the present invention is not limited to these examples. Each analysis condition in the examples is as described below.

<Analysis Condition 1: Volume Average Particle Diameter>

The volume average particle diameter of each particle was measured by a laser diffraction scattering particle size distribution measuring device (Beckman Coulter LS13 320).

<Analysis Condition 2: Measurement of Molecular Weight of Chain Polymer>

The molecular weight of chain polymer was measured after releasing chain polymers from particles by hydrolysis using an aqueous solution of sodium hydroxide.

That is, 1 g of particles was dispersed in 4 g of an aqueous solution of sodium hydroxide (1 N, pH 14), and the obtained mixture was stirred at 25° C. for 3 hours to release chain polymers from the particles. The particles were separated using magnetism, and the supernatant in which the chain polymers had been dissolved was collected. Next, to this chain polymer solution was added 1 M hydrochloric acid until the pH of the solution became 7 to neutralize the solution. In order to be used in calculating the weight of chain polymer, the weight of sodium chloride thus produced was calculated from the weight of 1 M hydrochloric acid added. Then, the solution after neutralization was freeze-dried to obtain the chain polymer including sodium chloride as powders. In order to be used in calculating the weight of chain polymer, the weight of powder was measured.

Using the above powders as a test specimen, the Mn and Mw of chain polymer formed on the surface of particles were measured under the following conditions by gel permeation chromatography (GPC), using TSKgel G3000 PIAIXL column manufactured by Tosoh Corporation and Chrom NAV chromatography data station program manufactured by JASCO International Co., Ltd.

(Measurement Conditions)
Flow rate: 0.8 mL/min
Eluting solvent: 0.2 M sodium phosphate buffer (pH 7.0)
Column temperature: 25° C.
Reference material: TSKgel standard Poly(ethylene oxide) SE-kit manufactured by Tosoh Corporation and Polyethylene Glycol 4,000 manufactured by Wako Pure Chemical Industries, Ltd.

<Analysis Condition 3: Polymer Density of Chain Polymer Occupying Surface of Particles>

The polymer density was calculated from the weight of the chain polymer released from particles, the number average molecular weight of the chain polymer, and the surface area of particles by the following formula.

[Density of chain polymer occupying surface of particles (chain polymers/nm$^2$)]=[Number of chain polymers binding to 1 g of particles (chain polymers)]/[Total surface area per g of particles (nm$^2$)]

Note that the methods for calculating the number of chain polymers binding to 1 g of particles and the total surface area per g of particles are as described below.

(Number of Chain Polymers Binding to 1 g of Particles)

The weight of chain polymer binding to 1 g of particles was calculated by the following formula ($\alpha$), and using the obtained value, the number of chain polymers binding to 1 g of particles was calculated by the following formulae ($\beta$) and ($\gamma$):

Weight of chain polymer binding to 1 g of particles (mg)=Weight of powder after freeze-drying (mg)−Weight of sodium chloride (mg)  ($\alpha$):

Number of chain polymers binding to 1 g of particles (mol)={Weight of chain polymer binding to 1 g of particles (mg)/Number average molecular weight of chain polymer (g/mol)}/1000  ($\beta$):

Number of chain polymers binding to 1 g of particles (chain polymers)=Number of chain polymers binding to 1 g of particles (mol)×6.02× 10$^{23}$ (Avogadro's number)  ($\gamma$):

(Total Surface Area Per g of Particles)

The total surface area was calculated by the following formulae ($\delta$) to ($\theta$). The specific gravity of particles in the formula ($\epsilon$) was calculated from the specific gravity of a polymer, the specific gravity of a magnetic substance, and the ratio of the polymer and the magnetic substance occupying particles.

Volume per particle ($\mu m^3$)=4/3×$\pi$×{Volume average radius of particles ($\mu m$)}$^3$  ($\delta$):

Mass per particle (g)=Volume per particle ($\mu m^3$)× Specific gravity of particles (g/$\mu m^3$)  ($\epsilon$):

Number of particles per g of particles (particles)=1 g/mass per particle (g)  ($\zeta$):

Surface area per particle (nm$^2$)=4×$\pi$×{Radius of particle (nm)}$^2$  ($\eta$):

Total surface area per g of particles (nm$^2$)=Surface area per particles (nm$^2$)×Number of particles per g of particles (particles)  ($\theta$):

<Analysis Condition 4: Content of Reactive Functional Group (Carboxy Group)>

The content of reactive functional group (carboxy group) per g of solid content in particles was obtained by measuring the content of reactive functional group (carboxy group) contained in chain polymers released from particles using conductometry (Metrohm, 794 Basic Titrino).

<Analysis Condition 5: Parking Area>

Parking area was obtained by dividing the surface area of the particles before binding of the chain polymer by the content of the reactive functional group (carboxy group).

<Analysis Condition 6: Content Ratio (a/b)>

The number of moles "a" and the number of moles "c" were calculated by the following method, and then, the number of moles "a" and the number of moles "c" were added up to calculate the number of moles "b". The content ratio (a/b) was obtained by these values.

(Number of Moles "a")

Number of moles "a"=Amount of reactive functional group (carboxy group) per g of particles (mol)/Number of polymers per g of particles (polymers)

(Number of Moles "c")

The number of moles "c" was calculated from the following formulae (A), (B) and (C).

Weight per g of particles in first structural unit (g)=Amount of reactive functional group (carboxy group) per g of particles (mol)×Molecular weight of first structural unit (g/mol)  (A):

Weight per g of particles in structural unit other than first structural unit (g)=Weight of chain polymer per g of particles (g)−Weight per g of particles in first structural unit (g)  (B):

Number of moles "c"={Weight per g of particles in structural unit other than first structural unit (g)/Molecular weight of structural unit other than first structural unit (g/mol)}/Number of polymers per g of particles (polymers)  (C):

Synthetic Example 1: Preparation of Magnetic Particles Having Hydroxy Groups on Surface With 20 g of a 1% by mass of aqueous solution of dodecyl sodium sulfate, 2 g of a 75% solution of di(3,5,5-trimethyl hexanoyl)peroxide ("PEROYL 355-75 (S)" manufactured by NOF Corporation) was mixed, and the obtained mixture was finely emulsified by an ultrasonic disperser. This was put into a reactor containing 13 g of polystyrene particles (number average particle diameter: 0.77 $\mu m$) and 41 g of water, and the mixture was stirred at 25° C. for 12 hours.

Subsequently, 96 g of styrene and 4 g of divinyl benzene were emulsified with 400 g of a 0.1% by mass of aqueous solution of sodium dodecyl sulfate (hereinafter, referred to as "SDS") in another container, and this was put into the above reactor, and the mixture was stirred at 40° C. for 2 hours, followed by raising the temperature to 75° C., and polymerization was carried out for 8 hours. After cooling to room temperature, only particles taken out by centrifugation were washed with water and dried. These particles were used as core particles (number average particle diameter: 1.5 μm).

Next, acetone was added to oily magnetic fluid ("EXP series, EMG", manufactured by Ferrotec Corporation) in another container to precipitate and deposit particles, and these were then dried to obtain ferrite magnetic fine particles having the surface hydrophobized (average primary particle diameter: 0.01 μm).

Subsequently, 15 g of the above core particles and 15 g of the above hydrophobized magnetic fine particles were mixed well by a mixer, and this mixture was treated using an NHS-0 type hybridization system (manufactured by Nara Machinery Co., Ltd.) at a circumferential velocity of wings (impeller) of 100 m/sec (16,200 rpm) for 5 minutes to obtain mother particles having a magnetic layer including the magnetic fine particles on the surface (number average particle diameter: 2.0 μm).

Next, 250 g of a 0.50% by mass of aqueous solution of SDS was charged into a 500 mL separable flask, and then 10 g of the above mother particles having a magnetic layer were added, and the obtained mixture was dispersed by a homogenizer and then heated to 60° C., and the temperature was maintained.

Subsequently, 75 g of a 0.50% by mass of aqueous solution of SDS, 13.5 g of methyl methacrylate (hereinafter, referred to as "MMA"), 1.5 g of trimethylolpropane trimethacrylate (hereinafter, referred to as "TMP"), and 0.3 g of a 75% solution of di(3,5,5-trimethyl hexanoyl)peroxide ("PEROYL 355-75 (S)" manufactured by NOF Corporation) were put into another container and dispersed to obtain a pre-emulsion. The entire amount of this pre-emulsion was added dropwise to the above 500 mL separable flask maintained at 60° C. over a period of 2 hours. After a dropwise addition, the mixture was maintained at 60° C. and stirred for an hour.

After that, 37.5 g of a 0.50% by mass of aqueous solution of SOS, 6.56 g of glycidyl methacrylate (hereinafter, referred to as "GMA"), 0.94 g of TMP, and 0.15 g of a 75% solution of di(3,5,5-trimethyl hexanoyl) peroxide ("PEROYL 355-75 (S)" manufactured by NOF Corporation) were put into another container and dispersed to obtain a pre-emulsion. The entire amount of this pre-emulsion was added dropwise to the above 500 mL separable flask maintained at 60° C. over a period of an hour and 20 minutes. After that, the temperature was raised to 75° C., then polymerization was continued for another 2 hours, and the reaction was completed. Subsequently, 10 mL of a 1 mol/L aqueous solution of sulfuric acid was put into this 500 mL separable flask, and the mixture was stirred at 60° C. for 6 hours. Then, the particles in the above 500 mL separable flask were separated using magnetism and then repeatedly washed with distilled water.

As described above, the magnetic particles having hydroxy groups on the surface were obtained.

Synthetic Example 2: Preparation of Magnetic Particles Having Atom Transfer Radical Polymerization Initiating Group on Surface Into a flask, 10 g of magnetic particles having hydroxy groups on the surface, obtained in Synthetic Example 1, were charged, and 32 mL of dehydrated tetrahydrofuran and 7.5 mL of triethylamine were added under a nitrogen flow, then the mixture was stirred. This flask was immersed in an ice bath, and thereto was added 6.3 mL of 2-bromoisobutyryl bromide dropwise over a period of 30 minutes. After a reaction at room temperature for 6 hours, the particles in the flask were separated using magnetism, and the particles were then redispersed in acetone. The magnetic separation and redispersion were carried out another several times, and the particles were then dispersed in a 0.10% by mass of aqueous solution of SDS. Br contained in the atom transfer radical polymerization initiating group (2-bromoisobutyryl group) was detected by a fluorescent X-ray analysis.

As described above, the magnetic particles having the atom transfer radical polymerization initiating group (2-bromoisobutyryl group) on the surface were obtained. These particles were named as particles (A).

Example 1: Preparation of Magnetic Particles in which Chain Polymer of Hydrophilic Random Copolymer Having Reactive Functional Group (Carboxy Group) Binds to Surface 1

The titled magnetic particles were prepared in accordance with the following synthetic route (Herein, ran in the formula means that two structural units adjacent thereto are a random polymer structure. The same shall apply hereafter). Specific procedures are shown below.

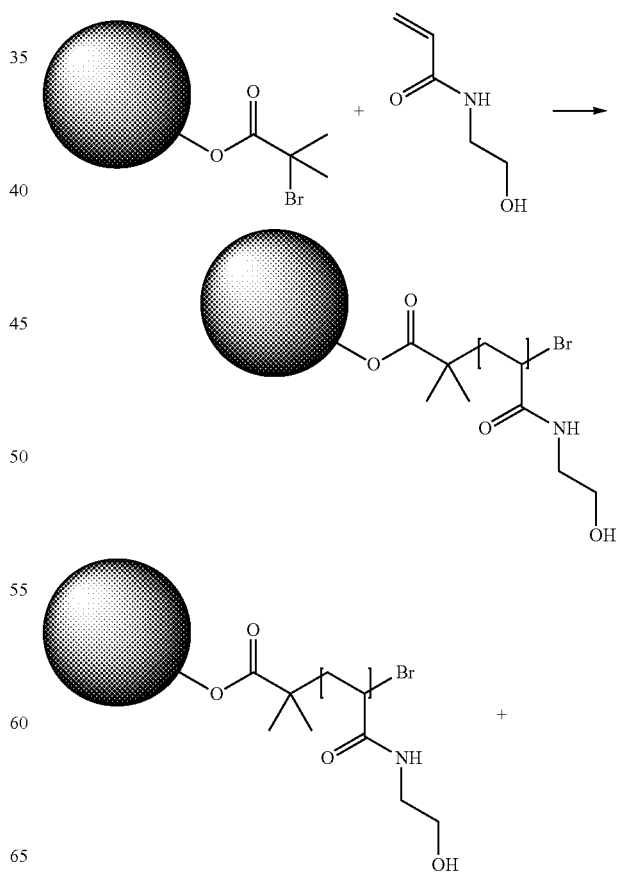

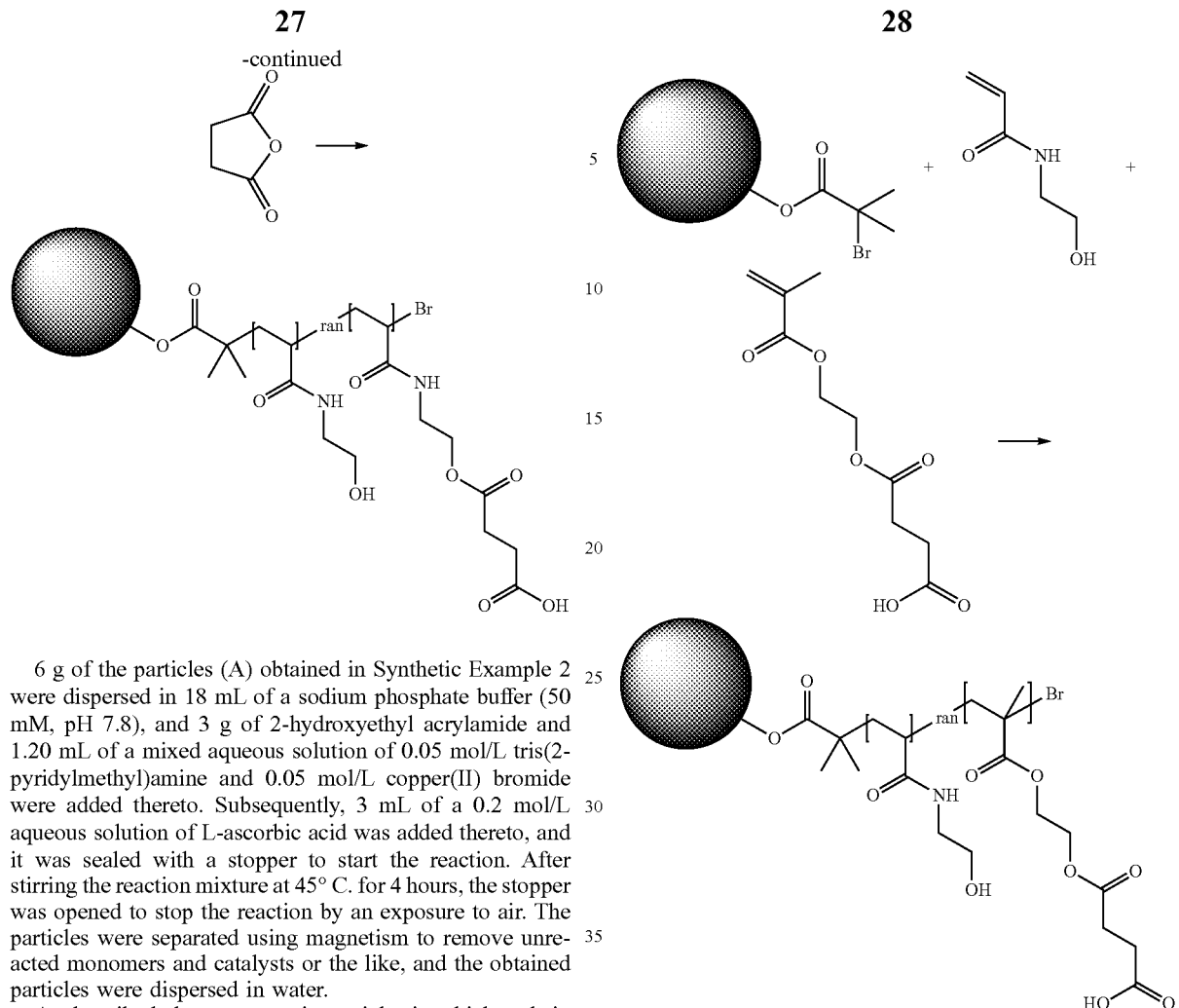

6 g of the particles (A) obtained in Synthetic Example 2 were dispersed in 18 mL of a sodium phosphate buffer (50 mM, pH 7.8), and 3 g of 2-hydroxyethyl acrylamide and 1.20 mL of a mixed aqueous solution of 0.05 mol/L tris(2-pyridylmethyl)amine and 0.05 mol/L copper(II) bromide were added thereto. Subsequently, 3 mL of a 0.2 mol/L aqueous solution of L-ascorbic acid was added thereto, and it was sealed with a stopper to start the reaction. After stirring the reaction mixture at 45° C. for 4 hours, the stopper was opened to stop the reaction by an exposure to air. The particles were separated using magnetism to remove unreacted monomers and catalysts or the like, and the obtained particles were dispersed in water.

As described above, magnetic particles in which a chain polymer constituted of a repeating unit derived from 2-hydroxyethyl acrylamide binds to the surface were obtained. These particles were named as particles (B).

Next, 1 g of the particles (B) was dispersed in 5 mL of dimethylsulfoxide, and a solution obtained by dissolving 0.2 mL of triethylamine and succinic anhydride in 4.8 mL of dimethylsulfoxide were added thereto, then the mixture was reacted at 25° C. for 4 hours. In order to prepare particles having different amounts of reactive functional group (carboxy group) in the chain polymer, this reaction was carried out with five levels of added amounts of succinic anhydride, 0.01 g, 0.02 g, 0.04 g, 0.08 g, and 0.16 g.

Thereafter, the particles were separated using magnetism, followed by dispersion in water.

As described above, magnetic particles in which a chain polymer of a hydrophilic random copolymer having a reactive functional group (carboxy group) binds to the surface were obtained. The obtained particles were named as particles (C) to (G), in the ascending order of the amount of reactive functional group (the amount of carboxy group).

Example 2; Preparation of Magnetic Particles in which Chain Polymer of Hydrophilic Random Copolymer Having Reactive Functional Group (Carboxy Group) Binds to Surface 2

The titled magnetic particles were prepared in accordance with the following synthetic route Specific procedures are shown below.

2 g of the particles (A) obtained in Synthetic Example 2 was dispersed in 6 mL of a mixed solution of a sodium phosphate buffer (50 mM, pH 7.8)/ethanol=1/1 (v/v), and a total of 1 g of 2-hydroxyethyl acrylamide and 2-methacryloyloxyethyl succinate, and further 0.40 mL of a mixed aqueous solution of 0.05 mol/L tris(2-pyridylmethyl)amine and 0.05 mol/L copper(II) bromide were added thereto. Subsequently, 1 mL of a 0.2 mol/L aqueous solution of L-ascorbic acid was added thereto, and it was sealed with a stopper to start the reaction. In order to prepare particles having different amounts of reactive functional group (carboxy group) in the chain polymer, this reaction was carried out with three levels of mixing ratios of 2-hydroxyethyl acrylamide/2-methacryloyloxyethyl succinate, 1/1 (w/w), 4/1 (w/w), and 9/1 (w/w). After stirring the reaction mixture at 45° C. for 4 hours, the stopper was opened to stop the reaction by an exposure to air.

Thereafter, the particles were separated using magnetism to remove unreacted monomers and catalysts or the like, and the obtained particles were dispersed in water.

As described above, magnetic particles in which a chain polymer of a hydrophilic random copolymer having a reactive functional group (carboxy group) binds to the surface were obtained. The obtained particles were named as particles (H) to (J), in the ascending order of the amount of reactive functional group (the amount of carboxy group).

Example 3: Preparation of Magnetic Particles in which Chain Polymer of Hydrophilic Random Copolymer Having Reactive Functional Group (Carboxy Group) Binds to Surface 3

The titled magnetic particles were prepared in accordance with the following synthetic route Specific procedures are shown below.

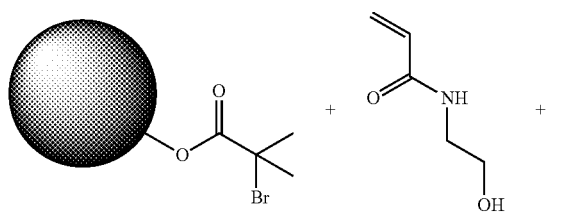

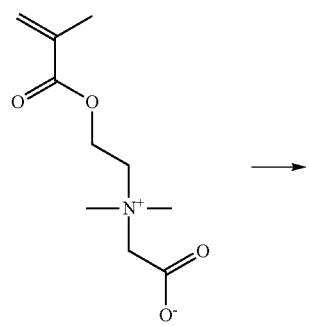

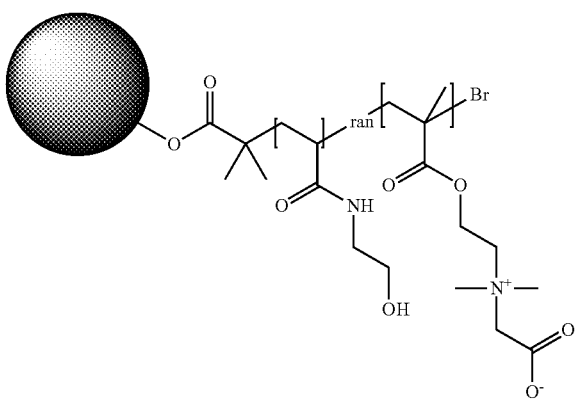

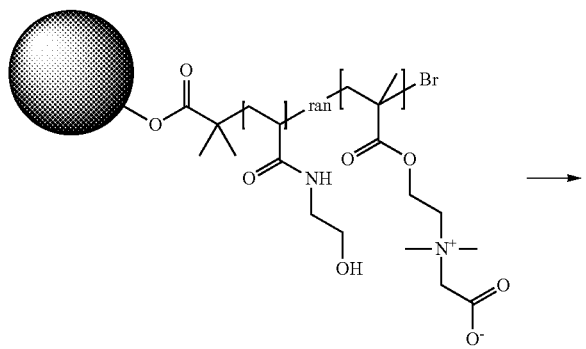

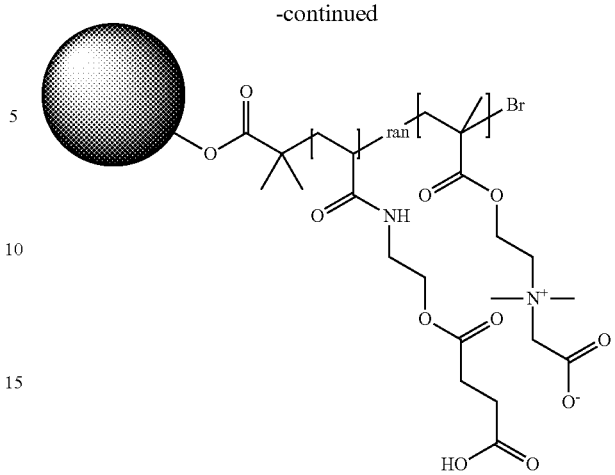

2 g of the particles (A) obtained in Synthetic Example 2 was dispersed in 6 mL of a sodium phosphate buffer (50 mM, pH 7.8), and a total of 0.5 g of N-methacryloyloxy-ethyl-N,N-dimethylammonium-α-N-methylcarboxybetaine and 2-hydroxyethyl acrylamide, and further 0.40 mL of a mixed aqueous solution of 0.05 mol/L tris(2-pyridylmethyl) amine and 0.05 mol/L copper(II) bromide were added thereto. Subsequently, 1 mL of a 0.2 mol/L aqueous solution of L-ascorbic acid was added thereto, and it was sealed with a stopper to start the reaction. This reaction was carried out with two levels of mixing ratios of N-methacryloyloxyethyl-N,N-dimethylammonium-α-N-methylcarboxybetaine/2-hydroxyethyl acrylamide, 1/1 (w/w) and 4/1 (w/w). After stirring the reaction mixture at 45° C. for 4 hours, the stopper was opened to stop the reaction by an exposure to air.

Thereafter, the particles were separated using magnetism to remove unreacted monomers and catalysts or the like, and the obtained particles were dispersed in water.

Next, 1.5 g of the obtained particles was dispersed in 8 mL of dimethylsulfoxide, and a solution obtained by dissolving 0.3 mL of triethylamine and 1.5 g of succinic anhydride in 7.2 mL of dimethylsulfoxide was added thereto. The mixture was reacted at 25° C. for 4 hours, thereby introducing a reactive functional group (carboxy group), then the particles were separated using magnetism, and the obtained particles were dispersed in water.

As described above, magnetic particles in which a chain polymer of a hydrophilic random copolymer having a reactive functional group (carboxy group) binds to the surface were obtained. The obtained particles were named as particles (K) to (L), in the ascending order of the amount of reactive functional group (the amount of carboxy group).

Example 4: Preparation of Magnetic Particles in which Chain Polymer Containing Hydrophilic Random Copolymer Structure Having Reactive Functional Group (Carboxy Group) Binds to Surface The titled magnetic particles were prepared in accordance with the following synthetic route Specific procedures are shown below.

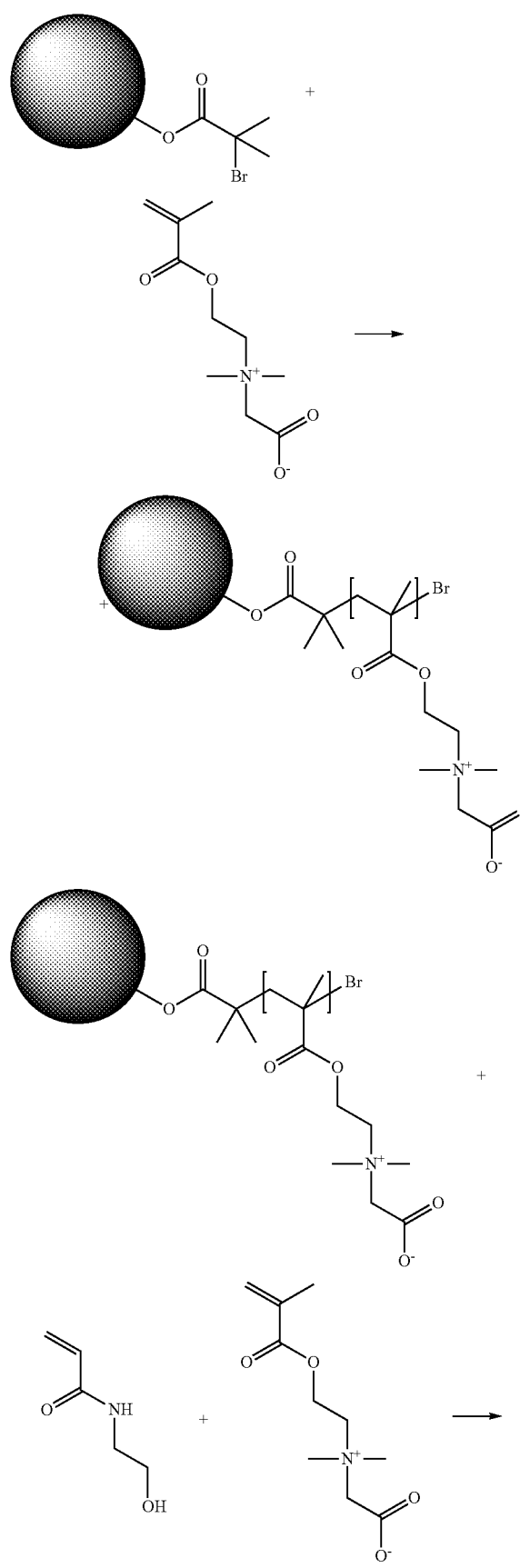

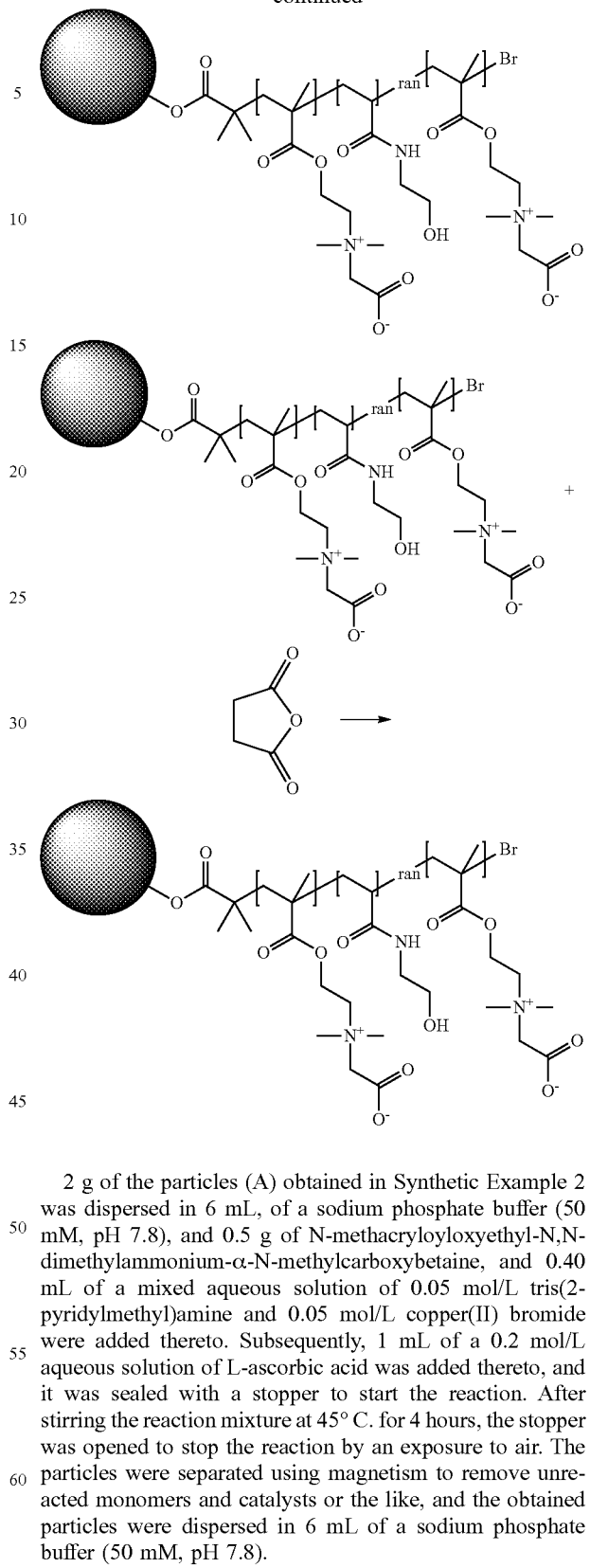

2 g of the particles (A) obtained in Synthetic Example 2 was dispersed in 6 mL, of a sodium phosphate buffer (50 mM, pH 7.8), and 0.5 g of N-methacryloyloxyethyl-N,N-dimethylammonium-α-N-methylcarboxybetaine, and 0.40 mL of a mixed aqueous solution of 0.05 mol/L tris(2-pyridylmethyl)amine and 0.05 mol/L copper(II) bromide were added thereto. Subsequently, 1 mL of a 0.2 mol/L aqueous solution of L-ascorbic acid was added thereto, and it was sealed with a stopper to start the reaction. After stirring the reaction mixture at 45° C. for 4 hours, the stopper was opened to stop the reaction by an exposure to air. The particles were separated using magnetism to remove unreacted monomers and catalysts or the like, and the obtained particles were dispersed in 6 mL of a sodium phosphate buffer (50 mM, pH 7.8).

Next, a total of 0.5 g of N-methacryloyloxyethyl-N,N-dimethylammonium-α-N-methylcarboxybetaine/2-hydroxyethyl acrylamide=1/1 (w/w), and 0.40 mL of a mixed aqueous solution of 0.05 mol/L tris(2-pyridylmethyl)amine and 0.05 mol/L copper(II) bromide were added thereto. Subsequently, 1 mL of a 0.2 mol/L aqueous solution of L-ascorbic acid was added thereto, and it was sealed with a stopper to start the reaction. After stirring the reaction mixture at 45° C. for 1 hour, the stopper was opened to stop the reaction by an exposure to air. The particles were separated using magnetism to remove unreacted monomers and catalysts or the like, and the obtained particles were dispersed in water.

Next, 1.5 g of the obtained particles was dispersed in 8 mL of dimethylsulfoxide, and a solution obtained by dissolving 0.3 mL of triethylamine and 1.5 g of succinic anhydride in 7.2 mL of dimethylsulfoxide was added thereto. The mixture was reacted at 25° C. for 4 hours, thereby introducing a reactive functional group (carboxy group), then the particles were separated using magnetism, and the obtained particles were dispersed in water.

As described above, magnetic particles in which a chain polymer containing a hydrophilic random copolymer structure having a reactive functional group (carboxy group) binds to the surface were obtained. The obtained particles were named as particles (M).

Comparative Example 1: Preparation of Reactive Functional Group (Carboxy Group)-Containing Magnetic Particles Having No Chain Polymer 1 g of the magnetic particles having hydroxy groups on the surface obtained in Synthetic Example 1 was dispersed in 4.8 mL of 1,3-dioxolane, and a solution obtained by dissolving 0.2 mL of triethylamine and 0.08 g of succinic anhydride in 4.8 mL of 1,3-dioxolane was added thereto. The mixture was reacted at 25° C. for 4 hours, then the particles were separated using magnetism, and dispersed in water.

As described above, reactive functional group (carboxy group)-containing magnetic particles having no chain polymer was obtained. The obtained particles were named as particles (X).

Comparative Example 2: Preparation of Magnetic Particles in which Chain Polymer of Block Copolymer Binds to Surface 2 g of the particles (A) obtained in Synthetic Example 2 was dispersed in 6 mL of a sodium phosphate buffer (50 mM, pH 7.8), and 0.5 g of N-methacryloyloxyethyl-N,N-dimethylammonium-α-N-methylcarboxybetaine, and 0.40 mL of a mixed aqueous solution of 0.05 mol/L tris(2-pyridylmethyl)amine and 0.05 mol/L copper(II) bromide were added thereto. Subsequently, 1 mL of a 0.2 mol/L aqueous solution of L-ascorbic acid was added thereto, and it was sealed with a stopper to start the reaction. After stirring the reaction mixture at 45° C. for 4 hours, the stopper was opened to stop the reaction by an exposure to air. The particles were separated using magnetism to remove unreacted monomers and catalysts or the like, and the obtained particles were dispersed in 6 mL of a sodium phosphate buffer (50 mM, pH 7.8).

Next, 0.5 g of 2-hydroxyethyl acrylamide and 0.40 mL of a mixed aqueous solution of 0.05 mol/L tris(2-pyridylmethyl)amine and 0.05 mol/L copper(II) bromide were added thereto. Subsequently, 1 mL of a 0.2 mol/L aqueous solution of L-ascorbic acid was added thereto, and it was sealed with a stopper to start the reaction. After stirring the reaction mixture at 45° C. for a certain time (1 hour or 30 minutes), the stopper was opened to stop the reaction by an exposure to air. The particles were separated using magnetism to remove unreacted monomers and catalysts or the like, and the obtained particles were dispersed in water.

Next, 1.5 g of the obtained particles was dispersed in 8 mL of dimethylsulfoxide, and a solution obtained by dissolving 0.3 mL of triethylamine and 1.5 g of succinic anhydride in 7.2 mL of dimethylsulfoxide was added thereto. The mixture was reacted at 25° C. for 4 hours, thereby introducing a reactive functional group (carboxy group), then the particles were separated using magnetism, and the obtained particles were dispersed in water.

As described above, magnetic particles in which a chain polymer of a block copolymer binds to the surface were obtained. As to the obtained particles, the particles obtained with the certain time of 1 hour were named as particles (Y), and the particles obtained with the certain time of 30 minutes were named as particles M.

Comparative Example 3: Preparation of Magnetic Particles in which Hydrophilic Chain Homopolymer Having No Carboxy Group Binds to Surface 6 g of the particles (A) obtained in Synthetic Example 2 were dispersed in 18 mL of a sodium phosphate buffer (50 mM, pH 7.8), and 3 g of 2-hydroxyethyl acrylamide and 1.20 mL of a mixed aqueous solution of 0.05 mol/L tris(2-pyridylmethyl)amine and 0.05 mol/L copper(II) bromide were added thereto. Subsequently, 3 mL of a 0.2 mol/L aqueous solution of L-ascorbic acid was added thereto, and it was sealed with a stopper to start the reaction. After stirring the reaction mixture at 45° C. for 4 hours, the stopper was opened to stop the reaction by an exposure to air. The particles were separated using magnetism to remove unreacted monomers and catalysts or the like, and the obtained particles were dispersed in water.

As described above, magnetic particles in which a chain polymer constituted of a repeating unit derived from 2-hydroxyethyl acrylamide binds to the surface were obtained. These particles were named as particles (W).

As to the particles (C) to (M), (X) to (Z) and (W) obtained in each of the above examples and comparative examples, for example, volume average particle diameter and the molecular weight of the chain polymer were measured, in accordance with the analysis conditions as described above. The results are shown in Tables 1 to 2.

Test Examples 1 mg of the particles (C) to (M) and (W) to (Z) were dispersed was each charged into a 2-mL Eppendorf tube, and washed with a PBS(−) buffer. To each of the particles, 100 μL of a Jurkat cell lysate solution (containing 100 μg of protein impurities) was added, and the tubes were incubated for 30 minutes. The particles were then separated using magnetism to remove a supernatant, and the particles were washed 5 times with a TBS-T (0.05% by mass Tween 20) buffer. Next, an aqueous solution of sodium dodecylbenzenesulfonate (0.5% by mass) was added to each of the particles to detach nonspecifically adsorbing protein impurities from the particles. The amount of the nonspecifically adsorbing protein impurities was visually confirmed by SDS-polyacrylamide gel electrophoresis. The results are shown in Table 1.

Then, considering the amount of reactive functional group (the amount of carboxy group), an effect of suppressing nonspecific adsorption of each of the particles was evaluated in accordance with the following criteria. The results are shown in Table 2.

(Evaluation Criteria)

AA: Adsorption of protein impurities is not observed, very good

A: While the amount of reactive functional group is large, adsorption of protein impurities is not often observed, good B: Slight adsorption of protein impurities is confirmed, and it is considered that protein impurities adsorbed to many of the reactive functional group, considering the amount of reactive functional group, thus slightly poor C: Adsorption of protein impurities is clearly confirmed, poor

TABLE 1

| Particles | | Volume average particle diameter (μm) | Mn | Mw | Mw/Mn | Polymer density (polymers/nm²) |
|---|---|---|---|---|---|---|
| Example 1 | (C) | 3 | 26600 | 38800 | 1.5 | 1.0 |
| | (D) | 3 | 26600 | 38800 | 1.5 | 1.0 |
| | (E) | 3 | 26600 | 38800 | 1.5 | 1.0 |
| | (F) | 3 | 26600 | 38800 | 1.5 | 1.0 |
| | (G) | 3 | 26600 | 38800 | 1.5 | 1.0 |
| Example 2 | (H) | 3 | 12300 | 16900 | 1.4 | 1.0 |
| | (I) | 3 | 18500 | 20000 | 1.1 | 1.0 |
| | (J) | 3 | 22600 | 31000 | 1.4 | 1.0 |
| Example 3 | (K) | 3 | 18100 | 21700 | 1.3 | 1.0 |
| | (L) | 3 | 14500 | 16000 | 1.1 | 1.0 |
| Example 4 | (M) | 3 | 12000 | 14400 | 1.2 | 1.0 |
| Comparative Example 1 | (X) | 3 | — | — | — | — |
| Comparative Example 2 | (Y) | 3 | 13300 | 16000 | 1.2 | 1.0 |
| | (Z) | 3 | 15000 | 16500 | 1.1 | 1.0 |
| Comparative Example 3 | (W) | 3 | 26600 | 38800 | 1.5 | 1.0 |

TABLE 2

| Particles | | Amount of reactive functional group (μmol/g) | Parking area (Å²/reactive functional group) | Content Ratio (a/b) | Effect of suppressing nonspecific adsorption |
|---|---|---|---|---|---|
| Example 1 | (C) | 32 | 6.9 | 0.05 | AA |
| | (D) | 63 | 3.5 | 0.11 | AA |
| | (E) | 124 | 1.8 | 0.21 | AA |
| | (F) | 243 | 0.9 | 0.42 | A |
| | (G) | 370 | 0.6 | 0.63 | A |
| Example 2 | (H) | 45 | 4.9 | 0.20 | AA |
| | (I) | 66 | 3.4 | 0.19 | AA |
| | (J) | 148 | 1.5 | 0.40 | A |
| Example 3 | (K) | 65 | 3.4 | 0.23 | AA |
| | (L) | 178 | 1.2 | 0.63 | AA |
| Example 4 | (M) | 27 | 8.2 | 0.05 | AA |
| Comparative Example 1 | (X) | 10 | 22 | — | C |
| Comparative Example 2 | (Y) | 39 | 5.7 | 1.00 | B |
| | (Z) | 66 | 3.4 | 1.00 | B |
| Comparative Example 3 | (W) | 0 | +∞ | 0 | AA |

As shown in FIG. 1 and Table 2, each of the particles of examples greatly suppressed nonspecific adsorption of protein impurities, as compared to the particles of Comparative Example 1. This result is presumably caused by binding of the hydrophilic chain polymer to the surface of the particles.

Also, the particles (C), (D), (E), (H), (I), (K), (L) and (M) of examples greatly suppressed nonspecific adsorption of protein impurities, while the amount of reactive functional group (the amount of carboxy group) was equivalent or higher, as compared to the particles of Comparative Example 2. On the other hand, in the particles (F), (G) and (J) of examples, nonspecific adsorption of protein impurities was not much observed, while the amount of reactive functional group (the amount of carboxy group) was twice or more, as compared to the particles of Comparative Example 2. Namely, it can be said that, in the particles (F), (G) and (J) of examples, nonspecific adsorption to the reactive functional group is less than in the particles of Comparative Example 2.

Also, among the particles of examples, in those having a content ratio (a/b) of 0.35 or less (the particles (C), (D), (E), (H), (I), (K), and (M)), nonspecific adsorption of protein impurities was all extremely effectively suppressed.

Moreover, in the particles (K) to (M) of examples, nonspecific adsorption of protein impurities was effectively suppressed, even when the content ratio (a/b) was relatively high and exceeded 0.3. This result is presumably caused by a betaine skeleton contained in the chain polymer.

The invention claimed is:

1. A solid-phase carrier, comprising:
 a support; and
 a chain polymer bound to the support,
 wherein the chain polymer comprises a random polymer structure containing a first structural unit having a reactive functional group, and a second structural unit having no reactive functional group or having a reactive functional group with a reactivity lower than a reactivity of the reactive functional group of the first structural unit, and
 a ratio of the number of moles "a" of the reactive functional group in the first structural unit to the number of moles "b" of all structural units in the chain polymer, (a/b), is from 0.01 to 0.7.

2. The solid-phase carrier according to claim 1, wherein the second structural unit comprises a hydrophilic group.

3. The solid-phase carrier according to claim 2, wherein the hydrophilic group is chargeable under aqueous neutral conditions.

4. The solid-phase carrier according to claim 2, wherein the hydrophilic group has a zwitterionic structure.

5. The solid-phase carrier according to claim 1,
 wherein one end of the chain polymer binds to the support via a divalent linking group, and
 the divalent linking group is covalently bonded to a surface of the support, and is also covalently bonded to the chain polymer.

6. The solid-phase carrier according to claim 5, wherein the divalent linking group binds to the surface of the support via an ester bond.

7. The solid-phase carrier according to claim 1, wherein a density of the chain polymer occupying a surface of the support is 0.1 to 2 polymers/nm².

8. The solid-phase carrier according to claim 1, wherein a molecular weight distribution (Mw/Mn) of the chain polymer is 1.0 to 2.5.

9. The solid-phase carrier according to claim 1, wherein a number average molecular weight (Mn) of the chain polymer is from 1,000 to 100,000.

10. The solid-phase carrier according to claim 1, which is a particle.

11. The solid-phase carrier according to claim 1, wherein a content of the reactive functional group in the first structural unit is 1 to 500 μmol per one gram of a solid content of the solid-phase carrier.

12. The solid-phase carrier according to claim 1, wherein a value obtained by dividing a surface area of the support by a content of the reactive functional group in the first structural unit is 0.4 to 220 (Å$^2$/reactive functional group).

13. A ligand-bound solid-phase carrier, comprising:
a ligand; and
the solid-phase carrier of claim 1 bound to the ligand.

14. The ligand-bound solid-phase carrier according to claim 13, wherein the ligand is at least one selected from the group consisting of an antibody, an antigen, a nucleic acid, a nucleotide, a nucleoside, an oligonucleotide, a protein, a peptide, an amino acid, a polysaccharide, a saccharide, a glycoprotein, a lipid, a glycolipid, a vitamin, a drug, a substrate, a hormone, a neurotransmitter, a virus, and a cell.

15. A method for detecting or separating a target substance in a sample, comprising:
contacting the ligand-bound solid-phase carrier of claim 13 with the sample.

16. A method for producing a solid-phase carrier, comprising:
preparing a carrier having a polymerization initiating group on the surface thereof; and
forming, from the polymerization initiating group as a starting point, a chain polymer comprising a random polymer structure containing a first structural unit having a reactive functional group, and a second structural unit having no reactive functional group or having a reactive functional group with a reactivity lower than a reactivity of the reactive functional group of the first structural unit, such that a ratio of the number of moles "a" of the reactive functional group in the first structural unit to the number of moles "b" of all structural unit units in the chain polymer, (a/b), is from 0.01 to 0.7.

17. The method for producing a solid-phase carrier according to claim 16,
wherein the forming of the chain polymer comprises
polymerizing a monomer inducing the second structural unit, from the polymerization initiating group as the starting point, to form a polymer, and
randomly introducing the reactive functional group into a part of the side chain of the second structural unit constituting the polymer to form the first structural unit having the reactive functional group.

18. The method for producing a solid-phase carrier according to claim 16,
wherein the forming of the chain polymer comprises
randomly copolymerizing a monomer inducing the first structural unit and a monomer inducing the second structural unit, from the polymerization initiating group as the starting point.

19. The method for producing a solid-phase carrier according to claim 16,
wherein the forming of the chain polymer comprises
randomly copolymerizing a monomer having a hydroxy group or an amino group and a monomer having no hydroxy group and an amino group, from the polymerization initiating group as the starting point, to form a random polymer structure, and
introducing a reactive functional group into the structural unit having a hydroxy group or an amino group in the random polymer structure to form the first structural unit having a reactive functional group.

20. A method for producing a ligand-bound solid-phase carrier, comprising:
binding a ligand to the reactive functional group in the first structural unit of the solid-phase carrier produced in the method of claim 16.

* * * * *